US012721888B2

(12) United States Patent
Gangaiah et al.

(10) Patent No.: US 12,721,888 B2
(45) Date of Patent: Sep. 1, 2026

(54) IMMUNOGENIC PROBIOTIC COMPOSITIONS AND METHODS OF USE INCLUDING IN VACCINATION

(71) Applicant: BiomEdit, Inc., Indianapolis, IN (US)

(72) Inventors: Dharanesh Mahimapura Gangaiah, Fishers, IN (US); Arvind Kumar, Fishers, IN (US); Nallakannu Pillay Lakshmanan, Fishers, IN (US); Shrinivasrao Mane, Fishers, IN (US)

(73) Assignee: BiomEdit, Inc., Fishers, IN (US)

( * ) Notice: Subject to any disclaimer, the term of this patent is extended or adjusted under 35 U.S.C. 154(b) by 480 days.

(21) Appl. No.: 18/036,259

(22) PCT Filed: Nov. 10, 2021

(86) PCT No.: PCT/US2021/058779
§ 371 (c)(1),
(2) Date: May 10, 2023

(87) PCT Pub. No.: WO2022/103837
PCT Pub. Date: May 19, 2022

(65) Prior Publication Data

US 2024/0058440 A1 Feb. 22, 2024

Related U.S. Application Data

(60) Provisional application No. 63/111,979, filed on Nov. 10, 2020.

(51) Int. Cl.

| | |
|---|---|
| ***A61K 39/07*** | (2006.01) |
| ***A61K 35/741*** | (2015.01) |
| ***A61K 35/747*** | (2015.01) |
| ***A61K 39/09*** | (2006.01) |
| ***A61K 39/12*** | (2006.01) |
| ***A61K 39/215*** | (2006.01) |
| ***A61K 39/245*** | (2006.01) |
| ***A61K 39/39*** | (2006.01) |
| *A61K 35/00* | (2006.01) |
| *A61K 39/00* | (2006.01) |

(52) U.S. Cl.
CPC ............ *A61K 39/39* (2013.01); *A61K 35/747* (2013.01); *A61K 39/12* (2013.01); *A61K 39/215* (2013.01); *A61K 2035/115* (2013.01); *A61K 2039/542* (2013.01)

(58) Field of Classification Search
None
See application file for complete search history.

(56) References Cited

FOREIGN PATENT DOCUMENTS

| | | | | | |
|---|---|---|---|---|---|
| CN | 105219683 | A | * | 1/2016 | |
| WO | 2001/021200 | A1 | | 3/2001 | |
| WO | 2006/124630 | A1 | | 11/2006 | |
| WO | WO-2006124630 | A2 | * | 11/2006 | ............. A61K 39/39 |
| WO | 2020/163284 | A1 | | 8/2020 | |
| WO | 2020/163398 | A1 | | 8/2020 | |

OTHER PUBLICATIONS

WP_003670646.1. aminotransferase [Limosilactobacillus reuteri]. Dated Oct. 11, 2019.*
Sundararaman et al. Role of probiotics to combat viral infections with emphasis on COVID-19. Applied Microbiology and Biotechnology (2020) 104:8089-8104. Published online: Aug. 19, 2020.*
Ogawa et al. Oral immunoadjuvant activity of *Lactobacillus casei* subsp. casei in dextran-fed layer chickens. British Journal of Nutrition (2006), 95, 430-434.*
Genbank: CP027805.1 Limosilactobacillus reuteri strain WHH1689 chromosome, complete genome. Dated Apr. 26, 2018.*

* cited by examiner

*Primary Examiner* — Nianxiang Zou
(74) *Attorney, Agent, or Firm* — Hoffmann & Baron LLP

(57) ABSTRACT

The present invention provides probiotic compositions and methods for improving animal health, particularly improving and enhancing vaccine response. The probiotic compositions include one or more isolated strains of *Lactobacillus* species bacteria which colonizes the gastrointestinal tract to increase the health and enhance the immune system and immune response of an animal.

31 Claims, 10 Drawing Sheets

Specification includes a Sequence Listing.

| | 1 | 2 | 3 | 4 | 5 | 6 | 7 | 8 | 9 | 10 | 11 | 12 | 13 |
|---|---|---|---|---|---|---|---|---|---|---|---|---|---|
| Vaccination | No | No | No | No | No | No | No | IBV | IBV | IBV | No | IBV | No |
| Probiotic Treatment | 3632 | 3630 | No | No | 3632 | 3632 and 3630 | 3632 and 3630 | 3632 and 3630 | No | No | Bacillus | Bacillus | Bacillus |
| Challenge | No | No | No | IBV M41 | IBV M41 | IBV M41 | IBV M41 | IBV M41 | IBV M41 | No | IBV M41 | IBV M41 | No |

IMMUNOGENIC PROBIOTIC COMPOSITIONS AND METHODS OF USE INCLUDING IN VACCINATION

CROSS REFERENCE TO RELATED APPLICATIONS

The present application is a national stage application which claims priority from PCT Application No. PCT/US2021/058779 filed Nov. 10, 2021, which in turn claims priority from U.S. Provisional Application Ser. No. 63/111,979 filed Nov. 10, 2020. Applicant claims the benefits of 35 U.S.C. § 120 as to the PCT application and priority under 35 U.S.C. § 119 as to the said U.S. Provisional application, and the entire disclosures of all applications are incorporated herein by reference in their entireties.

SEQUENCE LISTING

This application contains a Sequence Listing, which was submitted in ASCII format via EFS-Web, and is hereby incorporated by reference in its entirety. The ASCII copy, created on 9 Nov. 2021, is named "2848-20 PCT Seq-Listing_ST25" and is 6,468,762 bytes in size.

FIELD OF THE INVENTION

The present invention relates to probiotic compositions and methods for improving animal health, particularly improving and enhancing vaccine response. The probiotic compositions include one or more isolated strains of *Lactobacillus* bacteria which colonizes the gastrointestinal tract to increase the health and enhance the immune system and immune response of an animal.

BACKGROUND

Direct fed microbials (DFMs), often also called probiotics, are microorganisms which colonize, at least temporarily, the gastrointestinal tract of an animal and provide some beneficial effect to that animal. The microorganisms can be bacterial species, for example those from the genera *Bacillus, Lactobacillus, Lactococcus*, and *Enterococcus*. The microorganisms can also be yeast or even molds. The microorganisms can be provided to an animal orally or mucosally or, in the case of birds for instance, ocunasally i.e., spray, or provided to a fertilized egg, i.e. in ovo.

The beneficial activity provided by DFMS or probiotics can be the synthesis of vitamins or other nutritional molecules needed for a healthy metabolism of the host animal. A DFM or probiotic can also protect the host animal from disease, disorders, or clinical symptoms caused by other, pathogenic microorganisms. For example, the DFM or probiotic may produce factors having inhibitory or cytotoxic activity against certain species of pathogens, such as deleterious or disease-causing bacteria or immunomodulatory activity, such as improving or enhancing immune response to foreign agent(s) or foreign antigen, such as with vaccines or antigen administration.

Vaccines provide a useful tool to prevent the spread of infectious diseases or treat diseases. However, development of vaccines to provide sustained immunity to particular infectious diseases can be laborious and time consuming. Individuals that are immunodeficient or immunocompromised may have a reduced or ineffective/insufficient immune response to a vaccine or administered antigen. Furthermore, duration of immunity may not be sufficient to provide effective protection against these diseases. Many challenges remain in developing safer and more effective vaccines against the more complex diseases.

Thus, there is a need to develop further, more efficient, technologies for eliciting an efficient immune response.

SUMMARY OF THE INVENTION

The invention provides methods for stimulating an immune response, for vaccinating a subject for an infectious respiratory disease, for increasing antibody titer in a subject, including upon or with vaccination to said subject, for enhancing an immune response in a subject administered a vaccine, particularly an infectious respiratory virus vaccine, all and any of which include administration of an effective amount of an immunogenic probiotic composition comprising at least one *Lactobacillus reuteri* strain. In embodiments of the methods, a combination of two or at least two *Lactobacillus reuteri* strains are administered.

In one embodiment, the present disclosure provides a method of stimulating an immune response in a subject. In one embodiment, the present disclosure provides a method of enhancing, increasing or improving an immune response in a subject. The method includes administering an effective amount of an immunogenic probiotic composition comprising at least one *Lactobacillus reuteri* strain. In an embodiment, the method includes administering an effective amount of an immunogenic probiotic composition comprising at least one *Lactobacillus reuteri* strain wherein the at least one *Lactobacillus reuteri* strain comprises at least one sequence selected from SEQ ID NO:1-55 and sequences having at least 98%, at least 98.5%, at least 99%, or at least 99.5% sequence identity with at least one of SEQ ID NO:1-55. In an embodiment, the method comprises administering an effective amount of an immunogenic probiotic composition comprising at least one *Lactobacillus reuteri* strain, and optionally, an infectious disease vaccine, particularly an infectious respiratory disease vaccine, to a subject.

In one embodiment, the present disclosure provides a method of vaccinating a subject for an infectious respiratory disease. The method includes administering an effective amount of an immunogenic probiotic composition comprising at least one *Lactobacillus reuteri* strain and wherein the at least one *Lactobacillus reuteri* strain comprises at least one sequence selected from SEQ ID NO:1-55 and sequences having at least 98%, at least 98.5%, at least 99%, or at least 99.5% sequence identity with at least one of SEQ ID NO:1-55, and an infectious respiratory disease vaccine to a subject.

In an embodiment of the method(s), a combination of two isolated *Lactobacillus reuteri* strains are administered. In embodiments, an infectious respiratory disease vaccine is administered in combination with the at least one *Lactobacillus reuteri* strain or with the two isolated *Lactobacillus reuteri* strains. The at least one or the two *Lactobacillus reuteri* strains may be administered prior to a vaccine; may be administered prior to and in conjunction with a vaccine; may be administered prior to, in conjunction with, and following a vaccine; or may be administered in combination with or shortly following a vaccine. A vaccine may be administered as a single dose or multiple doses. The at least one or the two *Lactobacillus reuteri* strains may be administered prior to and/or between and/or in combination with a vaccine dose or multiple vaccine doses.

In an embodiment of the method(s) of the invention, a combination of two isolated *Lactobacillus reuteri* strains includes or comprises or is a combination of a first isolated

*Lactobacillus reuteri* strain and a second isolated *Lactobacillus reuteri* strain. In one embodiment, the isolated first *Lactobacillus reuteri* strain includes at least one of: a nucleic acid sequence having at least 95%, at least 96%, at least 97%, at least 98%, or at least 99% sequence identity with SEQ ID NO:26, a nucleic acid sequence having at least 95%, at least 96%, at least 97%, at least 98%, or at least 99% sequence identity with SEQ ID NO: 1, a nucleic acid sequence having at least 95%, at least 96%, at least 97%, at least 98%, or at least 99% sequence identity with SEQ ID NO: 3, and a nucleic acid that encodes for an amino acid sequence having at least 95%, at least 96%, at least 97%, at least 98%, or at least 99% sequence identity with SEQ ID NO: 8.

In one embodiment, the second isolated second *Lactobacillus reuteri* strain includes at least one of: a nucleic acid sequence having at least 95%, at least 96%, at least 97%, at least 98%, or at least 99% sequence identity with SEQ ID NO:25, a nucleic acid sequence having at least 95%, at least 96%, at least 97%, at least 98%, or at least 99% sequence identity with SEQ ID NO: 27, a nucleic acid sequence having at least 95%, at least 96%, at least 97%, at least 98%, or at least 99% sequence identity with SEQ ID NO: 28, and a nucleic acid sequence having at least 95%, at least 96%, at least 97%, at least 98%, or at least 99% sequence identity with SEQ ID NO: 29.

In one embodiment, the isolated first *Lactobacillus reuteri* strain has a nucleic acid or amino acid sequence including at least one of SEQ ID NOs: 1-24, 26, and 49-55, sequences having at least one nucleic acid or amino acid sequence difference from the sequence of at least one of SEQ ID NOs: 1-24, 26, and 49-55, sequences having one or more nucleic acid or amino acid sequence difference from the sequence of at least one of SEQ ID NOs: 1-24, 26, and 49-55, sequences having at least one nucleic acid or amino acid sequence difference from the sequence of at least one of SEQ ID NOs: 1-24, 26, and 49-55 and further having at least 99% sequence identity with at least one of SEQ ID NOs: 1-24, 26, and 49-55, sequences having at least one nucleic acid or amino acid sequence difference from the sequence of at least one of SEQ ID NOs: 1-24, 26, and 49-55 and further having at least 99% sequence identity with one or more of SEQ ID NOs: 1-24, 26, and 49-55, sequences having at least 98%, at least 98.5%, at least 99%, or at least 99.5% sequence identity with at least one of SEQ ID NOs: 1-24, 26, and 49-55. In one embodiment, the isolated first *Lactobacillus reuteri* strain has a genomic nucleic acid sequence including at least one of SEQ ID NOs: 49-55, sequences having one or more nucleic acid sequence difference from the sequence of at least one of SEQ ID NOs: 49-55, sequences having at least one nucleic acid sequence difference from the sequence of at least one of SEQ ID NOs: 49-55 and further having at least 97%, at least 98%, at least 99% or at least 99.5% sequence identity with one or more of SEQ ID NOs: 49-55, sequences having at least 98%, at least 98.5%, at least 99%, or at least 99.5% sequence identity to SEQ ID NOs: 49-55.

In an embodiment, the isolated first *Lactobacillus reuteri* strain is *Lactobacillus reuteri* strain 3632, which corresponds to ATCC Patent Deposit Number PTA-126788.

In one embodiment, the isolated first *Lactobacillus reuteri* strain comprises or has a genomic nucleic acid sequence corresponding to the genomic nucleic acid sequence of ATCC strain PTA-126788, or a variant thereof comprising or having a nucleic acid sequence at least 98%, at least 98.5%, at least 99%, or at least 99.5% sequence identity to the genomic nucleic acid sequence of ATCC strain PTA-126788.

In some embodiments, the isolated second *Lactobacillus reuteri* strain has a nucleic acid sequence or amino acid sequence including at least one of SEQ ID NOs: 25, 27-43, and 44-48, sequences having at least 98%, at least 98.5%, at least 99%, or at least 99.5% sequence identity with at least one of SEQ ID NOs: 25, 27-43, and 44-48.

In one embodiment, the isolated second *Lactobacillus reuteri* has a nucleic acid or amino acid sequence including at least one of SEQ ID NOs: 25, 27-43, and 44-48, sequences having at least one nucleic acid or amino acid sequence difference from the sequence of at least one of SEQ ID NOs: 25, 27-43, and 44-48, sequences having one or more nucleic acid or amino acid sequence difference from the sequence of at least one of SEQ ID NOs: 25, 27-43, and 44-48, sequences having at least one nucleic acid or amino acid sequence difference from the sequence of at least one of SEQ ID NOs: 25, 27-43, and 44-48 and further having at least 99% sequence identity with at least one of SEQ ID NOs: 25, 27-43, and 44-48, sequences having at least one nucleic acid or amino acid sequence difference from the sequence of at least one of SEQ ID NOs: 25, 27-43, and 44-48 and further having at least 99% sequence identity with one or more of SEQ ID NOs: 25, 27-43, and 44-48, sequences having at least 98%, at least 98.5%, at least 99%, or at least 99.5% sequence identity with at least one of SEQ ID NOs: 25, 27-43, and 44-48. In one embodiment, the isolated second *Lactobacillus reuteri* strain has a genomic nucleic acid sequence including at least one of SEQ ID NOs: 44-48, sequences having one or more nucleic acid sequence difference from the sequence of at least one of SEQ ID NOs: 44-48, sequences having at least one nucleic acid sequence difference from the sequence of at least one of SEQ ID NOs: 44-48 and further having at least 97%, at least 98%, at least 99% or at least 99.5% sequence identity with one or more of SEQ ID NOs: 44-48, sequences having at least 98%, at least 98.5%, at least 99%, or at least 99.5% sequence identity to SEQ ID NOs: 44-48.

In an embodiment, the second *Lactobacillus reuteri* is *Lactobacillus reuteri* strain 3630, which corresponds to ATCC Patent Deposit Number PTA-126787.

In one embodiment, the isolated second *Lactobacillus reuteri* strain comprises or has a genomic nucleic acid sequence corresponding to the genomic nucleic acid sequence of ATCC strain PTA-126787, or a variant thereof comprising or having a nucleic acid sequence at least 98%, at least 98.5%, at least 99%, or at least 99.5% sequence identity to the genomic nucleic acid sequence of ATCC strain PTA-126787.

In one embodiment, the present disclosure provides a method of increasing antibody titer in a subject. The method includes administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO: 1-55, and an infectious respiratory disease vaccine to a subject. The method includes administering an effective amount of an immunogenic probiotic composition comprising two isolated *Lactobacillus reuteri* strains, a first *Lactobacillus reuteri* strain and a second *Lactobacillus reuteri* strain, wherein the first *Lactobacillus reuteri* strain comprises at least one sequence selected from SEQ ID NO: 1-24, 26, and 49-55 and sequences having at least 98%, at least 98.5%, at least 99%, or at least 99.5% sequence identity with at least one of SEQ ID NO: 1-24, 26, and 49-55, wherein the second

*Lactobacillus reuteri* strain comprises at least one sequence selected from SEQ ID NO: 25, 27-43, and 44-48 and sequences having at least 98%, at least 98.5%, at least 99%, or at least 99.5% sequence identity with at least one of SEQ ID NO: 25, 27-43, and 44-48 and an infectious respiratory disease vaccine to a subject.

In one embodiment, the present disclosure provides a method of decreasing viral load in a subject. The method includes administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO: 1-55, and optionally, an infectious respiratory disease vaccine to a subject. The method includes administering an effective amount of an immunogenic probiotic composition comprising two isolated *Lactobacillus reuteri* strains, a first *Lactobacillus reuteri* strain and a second *Lactobacillus reuteri* strain, wherein the first *Lactobacillus reuteri* strain comprises at least one sequence selected from SEQ ID NO: 1-24, 26, and 49-55 and sequences having at least 98%, at least 98.5%, at least 99%, or at least 99.5% sequence identity with at least one of SEQ ID NO: 1-24, 26, and 49-55, wherein the second *Lactobacillus reuteri* strain comprises at least one sequence selected from SEQ ID NO: 25, 27-43, and 44-48 and sequences having at least 98%, at least 98.5%, at least 99%, or at least 99.5% sequence identity with at least one of SEQ ID NO: 25, 27-43, and 44-48 and an infectious respiratory disease vaccine to a subject.

In one embodiment, the present disclosure provides a method of stimulating an immune response in a subject. The method includes administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity thereto, and optionally, an infectious respiratory disease vaccine to a subject. The method includes administering an effective amount of an immunogenic probiotic composition comprising two isolated *Lactobacillus reuteri* strains, a first *Lactobacillus reuteri* strain and a second *Lactobacillus reuteri* strain, wherein the first *Lactobacillus reuteri* strain comprises at least one sequence selected from SEQ ID NO: 1-24, 26, and 49-55 and sequences having at least 98%, at least 98.5%, at least 99%, or at least 99.5% sequence identity with at least one of SEQ ID NO: 1-24, 26, and 49-55, wherein the second *Lactobacillus reuteri* strain comprises at least one sequence selected from SEQ ID NO: 25, 27-43, and 44-48 and sequences having at least 98%, at least 98.5%, at least 99%, or at least 99.5% sequence identity with at least one of SEQ ID NO: 25, 27-43, and 44-48 and an infectious respiratory disease vaccine to a subject.

In one embodiment, the present disclosure provides an immunogenic probiotic composition. The composition includes at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO: 1-55, and a pharmaceutically acceptable carrier. In an embodiment, the immunogenic probiotic composition comprises two isolated *Lactobacillus reuteri* strains, a first *Lactobacillus reuteri* strain and a second *Lactobacillus reuteri* strain, wherein the first *Lactobacillus reuteri* strain comprises at least one sequence selected from SEQ ID NO: 1-24, 26, and 49-55 and sequences having at least 98%, at least 98.5%, at least 99%, or at least 99.5% sequence identity with at least one of SEQ ID NO: 1-24, 26, and 49-55, wherein the second *Lactobacillus reuteri* strain comprises at least one sequence selected from SEQ ID NO: 25, 27-43, and 44-48 and sequences having at least 98%, at least 98.5%, at least 99%, or at least 99.5% sequence identity with at least one of SEQ ID NO: 25, 27-43, and 44-48.

DETAILED DESCRIPTION

Figure 1:
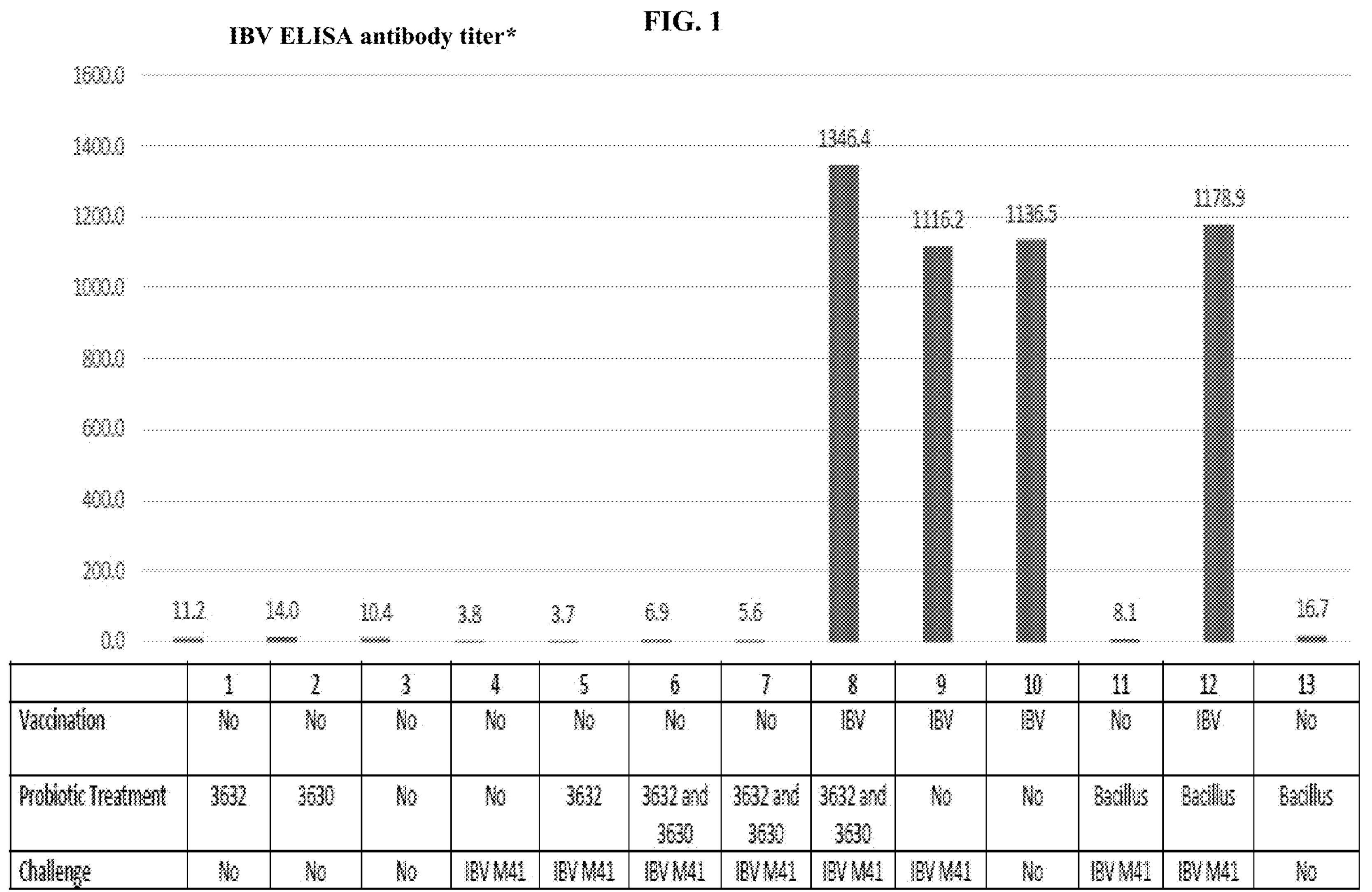
FIG. 1 depicts the effect of *Lactobacillus reuteri* cells on infectious bronchitis vaccine serology. Blood samples were collected for serology on Study day 24. Approximately 20% increase in antibody titer is observed when 3630 and 3630 are administered.

The present disclosure provides immunogenic probiotic compositions and methods of use.

In one embodiment, the invention provides an immunogenic probiotic composition including at least one isolated *Lactobacillus reuteri* strain. The at least one *Lactobacillus reuteri* strain includes at least one of a isolated first *Lactobacillus reuteri* strain and a isolated second *Lactobacillus reuteri* strain.

The at least one isolated *Lactobacillus reuteri* strain may include one *Lactobacillus reuteri* strain or a combination of two or more *Lactobacillus reuteri* strains. The *Lactobacillus reuteri* strains may have been selected for gut adaptation in poultry. The *Lactobacillus reuteri* strains may be been isolated from poultry.

In one embodiment, the isolated first *Lactobacillus reuteri* has a nucleic acid or amino acid sequence including at least one of SEQ ID NOs: 1-24, 26, and 49-55, sequences having at least 98%, at least 98.5%, at least 99%, or at least 99.5% sequence identity with at least one of SEQ ID NOs: 1-24, 26, and 49-55. In one embodiment, the isolated first *Lactobacillus reuteri* has a nucleic acid genome sequence including at least one of SEQ ID NOs: 49-55, sequences having at least 98%, at least 98.5%, at least 99%, or at least 99.5% sequence identity with at least one of SEQ ID NOs: 49-55. In one embodiment, the isolated first *Lactobacillus reuteri* strain has a nucleic acid genome sequence comprising SEQ ID NOs: 49-55, or a sequence having at least 98%, at least 98.5%, at least 99%, or at least 99.5% sequence identity with SEQ ID NOs: 49-55.

In one embodiment, the isolated first *Lactobacillus reuteri* has a nucleic acid or amino acid sequence including at least one of SEQ ID NOs: 1-24, 26, and 49-55, sequences having at least one nucleic acid or amino acid sequence difference from the sequence of at least one of SEQ ID NOs: 1-24, 26, and 49-55, sequences having one or more nucleic acid or amino acid sequence difference from the sequence of at least one of SEQ ID NOs: 1-24, 26, and 49-55, sequences having at least one nucleic acid or amino acid sequence difference from the sequence of at least one of SEQ ID NOs: 1-24, 26, and 49-55 and further having at least 99% sequence identity with at least one of SEQ ID NOs: 1-24, 26, and 49-55, sequences having at least one nucleic acid or amino acid sequence difference from the sequence of at least one of SEQ ID NOs: 1-24, 26, and 49-55 and further having at least 99% sequence identity with one or more of SEQ ID NOs: 1-24, 26, and 49-55, sequences having at least 98%, at least 98.5%, at least 99%, or at least 99.5% sequence identity with at least one of SEQ ID NOs: 1-24, 26, and 49-55.

In a preferred embodiment, the isolated first *Lactobacillus reuteri* strain is *Lactobacillus reuteri* strain 3632. As used herein, "*Lactobacillus reuteri* strain 3632", "LR 3632", and "3632" "ATCC Patent Deposit Number PTA-126788", "strain PTA-126788", V and "PTA-126788" may be used interchangeably.

In some embodiments, the isolated second *Lactobacillus reuteri* strain has a nucleic acid sequence or amino acid sequence including at least one of SEQ ID NOs: 25, 27-43, and 44-48, sequences having at least 98%, at least 98.5%, at least 99%, or at least 99.5% sequence identity with at least one of SEQ ID NOs: 25, 27-43, and 44-48. In embodiments, the isolated second *Lactobacillus reuteri* strain has a nucleic acid genome sequence comprising SEQ ID NOs: 44-48, or a sequence having at least 98%, at least 98.5%, at least 99%, or at least 99.5% sequence identity with SEQ ID NOs: 44-48.

In one embodiment, the isolated second *Lactobacillus reuteri* has a nucleic acid or amino acid sequence including at least one of SEQ ID NOs: 25, 27-43, and 44-48, sequences having at least one nucleic acid or amino acid sequence difference from the sequence of at least one of SEQ ID NOs: 25, 27-43, and 44-48, sequences having one or more nucleic acid or amino acid sequence difference from the sequence of at least one of SEQ ID NOs: 25, 27-43, and 44-48, sequences having at least one nucleic acid or amino acid sequence difference from the sequence of at least one of SEQ ID NOs: 25, 27-43, and 44-48 and further having at least 99% sequence identity with at least one of SEQ ID NOs: 25, 27-43, and 44-48, sequences having at least one nucleic acid or amino acid sequence difference from the sequence of at least one of SEQ ID NOs: 25, 27-43, and 44-48 and further having at least 99% sequence identity with one or more of SEQ ID NOs: 25, 27-43, and 44-48, sequences having at least 98%, at least 98.5%, at least 99%, or at least 99.5% sequence identity with at least one of SEQ ID NOs: 25, 27-43, and 44-48.

In a preferred embodiment, the second *Lactobacillus reuteri* is *Lactobacillus reuteri* strain 3630. As used herein, "*Lactobacillus reuteri* strain 3630", "LR 3630", "3630", "ATCC Patent Deposit Number PTA-126787", "strain PTA-126787" and "PTA-126787" may be used interchangeably.

In a preferred embodiment, the at least one isolated *Lactobacillus reuteri* strain includes strain 3632 and 3630.

In an embodiment, the at least one isolated *Lactobacillus reuteri* strain is a combination of *Lactobacillus reuteri* strain 3632 and strain 3630. In an embodiment, a combination of two or more *Lactobacillus reuteri* strains is a combination of strain 3632 and strain 3630. In an embodiment, a combination of two or more *Lactobacillus reuteri* strains is a combination of strain PTA-126788 and PTA-126787.

In an embodiment, the isolated strains of the present disclosure are not genetically modified by recombinant or genetically engineered means.

In a preferred embodiment, the at least one isolated *Lactobacillus reuteri* strain is selected from strain 3632 and 3630. In a preferred embodiment, the composition, particularly an immunogenic probiotic composition, comprises a combination of isolated *Lactobacillus reuteri* strains 3632 and 3630. In a preferred embodiment, the composition, particularly an immunogenic probiotic composition, comprises a combination of isolated *Lactobacillus* strains PTA-126788 and PTA-126787. In a preferred embodiment, the composition, particularly an immunogenic probiotic composition, comprises a combination of isolated *Lactobacillus* strains PTA-126788 and PTA-126787 or a *lactobacillus* strain having at least 98% or 99% amino acid or nucleic acid identity to strain PTA-126788 and isolated *Lactobacillus* strain PTA-126788 and PTA-126787 or a *lactobacillus* strain having at least 99% amino acid or nucleic acid identity to strain PTA-126787. In a preferred embodiment, the composition, particularly an immunogenic probiotic composition, comprises a combination of isolated *Lactobacillus* strains PTA-126788 and PTA-126787 or a *lactobacillus* strain having at least 98% or at least 99% amino acid or nucleic acid identity to strain PTA-126788 and isolated *Lactobacillus* strains PTA-126788 and PTA-126787 or a *lactobacillus* strain having at least 98% or at least 99% amino acid or nucleic acid identity to strain PTA-126787, wherein the strains each and/or together have probiotic activity or capability. In a preferred embodiment, the composition, particularly an immunogenic probiotic composition, comprises a combination of isolated *Lactobacillus* strains PTA-126788 and PTA-126787 or a *lactobacillus* strain having at least 98% or at least 99% amino acid or nucleic acid identity to strain PTA-126788 and isolated *Lactobacillus* strains PTA-126788 and PTA-126787 or a *lactobacillus* strain having at least 98% or at least 99% amino acid or nucleic acid identity to strain PTA-126787, wherein the strains each and/or together have immunogenic probiotic activity or capability and capability and activity to improve animal health.

In some embodiments, compositions disclosed herein include an isolated first *Lactobacillus reuteri* strain and an isolated second *Lactobacillus reuteri* strain at a ratio of approximately 0.75-1.5:1. In a preferred embodiment, the composition includes about equal amounts of the isolated first *Lactobacillus reuteri* strain and the isolated second *Lactobacillus reuteri* strain, or approximately 1:1.

In an embodiment, the composition includes about equal amounts, such as equal amounts measured as CFU/kg or CFU/ml of the composition, of the isolated first *Lactobacillus reuteri* strain and the isolated second *Lactobacillus reuteri* strain, or approximately 1:1.

The compositions disclosed herein can be formulated as animal feed, feed additive, food ingredient, vaccine additive or ingredient, water additive, water-mixed additive, consumable solution, consumable spray additive, consumable solid, consumable gel, injection, or combinations thereof. In one embodiment, the composition includes water.

In some embodiments, the compositions disclosed herein includes the isolated first *Lactobacillus reuteri* strain in an amount of about $10^2$-$10^8$ CFU/kg of the composition, about $10^6$-$10^8$ CFU/kg of the composition, about $10^4$-$10^7$ CFU/kg of the composition, about $10^3$-$10^5$ CFU/kg of the composition, about $10^2$ CFU/kg of the composition, about $10^3$ CFU/kg of the composition, about $10^6$ CFU/kg of the composition, about $10^7$ CFU/kg of the composition, or about $10^8$ CFU/kg of the composition. In some embodiments, the compositions disclosed herein includes the isolated first *Lactobacillus reuteri* strain in an amount of about $10^2$-$10^8$ CFU/ml of the composition, about $10^6$-$10^8$ CFU/ml of the composition, about $10^4$-$10^7$ CFU/ml of the composition, about $10^3$-$10^5$ CFU/ml of the composition, about $10^3$ CFU/ml of the composition, about $10^4$ CFU/ml of the composition, about $10^5$ CFU/ml of the composition, about $10^6$ CFU/ml of the composition, about $10^7$ CFU/ml of the composition, or about $10^8$ CFU/ml of the composition.

In some embodiments, the compositions disclosed herein includes the isolated second *Lactobacillus reuteri* strain in an amount of about $10^2$-$10^8$ CFU/kg of the composition, about $10^6$-$10^8$ CFU/kg of the composition, about $10^4$-$10^7$ CFU/kg of the composition, about $10^3$-$10^5$ CFU/kg of the composition, about $10^2$ CFU/kg of the composition, about $10^3$ CFU/kg of the composition, about $10^6$ CFU/kg of the composition, about $10^7$ CFU/kg of the composition, or about $10^8$ CFU/kg of the composition. In some embodiments, the compositions disclosed herein includes the isolated second *Lactobacillus reuteri* strain in an amount of about $10^2$-$10^8$ CFU/ml of the composition, about $10^6$-$10^8$ CFU/ml of the composition, about $10^4$-$10^7$ CFU/ml of the composition, about $10^3$-$10^5$ CFU/ml of the composition, about 10 CFU/ml of the composition, about $10^4$ CFU/ml of the composition, about $10^5$ CFU/ml of the composition, about $10^6$ CFU/ml of the composition, about $10^7$ CFU/ml of the composition, or about $10^8$ CFU/ml of the composition.

In some embodiments, the immunogenic probiotic composition includes at least one *Lactobacillus reuteri* strain and an infectious disease vaccine. In some embodiments, the immunogenic probiotic composition includes at least one *Lactobacillus reuteri* strain and an infectious respiratory disease vaccine. In some embodiments, the immunogenic probiotic composition includes at least one *Lactobacillus reuteri* strain and an infectious respiratory virus vaccine.

In some embodiments, the immunogenic probiotic composition includes at least one *Lactobacillus reuteri* strain and does not include an infectious respiratory disease vaccine. The present disclosure also provides methods of increasing animal health, wherein the method includes administering an effective amount of the composition to an animal.

The composition disclosed herein and above increases animal health by providing positive health benefits when administered to an animal, as compared to an animal that has not been administered the composition. As used herein, "animal" includes bird, a human, or a non-human mammal. Specific examples of birds include poultry such as chickens or turkey. Specific examples of animal include chickens, turkey, dogs, cats, cattle and swine. The chicken may be a broiler chicken or egg-laying or egg-producing chicken. The animal may be a human. The animal may be a non-human mammal.

Positive health benefits include decreasing feed conversion ratio, increasing weight, increasing lean body mass, decreasing pathogen-associated lesion formation in the gastrointestinal tract, decreasing colonization of pathogens, reducing inflammation, and decreasing mortality rate. Positive immunogenic health benefits include increasing seroconversion in animals administered a vaccine, increasing antibody titer(s) against a pathogen in animals administered a vaccine against the pathogen, reducing viral load of a virus in an animal, enhancing or increasing the reduction of viral load in an animal immunized with a vaccine against the virus, improving resistance against a virus, reducing colonization of a virus present in a herd or flock or group of animals where some animals are vaccinated against the virus, reduction of virus mediated lesions in an animal with vaccination against the virus or in an animal subjected to or exposed to the virus, reducing fecal load of virus in an animal, reducing viral shedding in feces of an animal and decreasing mortality rate on exposure to a virus.

In some embodiments, the compositions disclosed herein decreases feed conversion ratio by at least 1%, at least 5%, at least 25%, or at least 50%. In some embodiments, the compositions disclosed herein increases poultry weight by at least 1%, at least 5%, at least 25%, or at least 50%. In some embodiments, the compositions disclosed herein decrease pathogen-associated lesion formation in the gastrointestinal tract by at least 1%, at least 5%, at least 25%, or at least 50%. In some embodiments, the compositions disclosed herein decrease pathogen colonization by at least 1%, at least 5%, at least 25%, or at least 50%. In some embodiments, the compositions disclosed herein reduce inflammation by at least 1%, at least 5%, at least 25%, or at least 50%. In some embodiments, the compositions disclosed herein decrease mortality rate by at least 1%, at least 5%, at least 25%, or at least 50%.

In some embodiments, the compositions disclosed herein increased seroconversion with vaccine administration by at least 1%, at least 5%, at least 10%, at last 20%, at least 25%, or at least 50%. In some embodiments, the compositions disclosed herein increased virus specific antibody levels with vaccine administration by at least 5%, at least 10%, at last 20%, at least 25%, at least 50%, at least 60%, up to 100%. In some embodiments, the compositions disclosed herein reduced virus shedding in feces by at least 10 fold, at least 20 fold, at least 50 fold, at last 100 fold, at least 200 fold, over 100 fold, or over 200 fold.

In some embodiments, following values may be combined in any manner to create a minima, a maxima, or a range for decreasing feed conversion ratio, increasing poultry weight, increasing lean body mass, decreasing pathogen-associated lesion formation in the gastrointestinal tract, decreasing colonization of pathogens, and decreasing mortality rate, 1%, 5%, 25%, 50%, and 75%.

For example, the decrease in pathogen-associated lesion formation may be decreased by approximately 1% to 5%, and more preferably between approximately 5% to 50%.

In an embodiment, the composition of the inventions can be used as an immune modulator, an immunostimulant or an adjuvant. The composition of one or more *L reuteri* strain may be combined with one or more other or alternative immune modulator, immunostimulant or adjuvant. Immune modulators or immune stimulants may include cytokines or hormones which stimulate the immune response. An adjuvant may include, but is not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide.

As used herein, a bacterial pathogen includes *Salmonella, Clostridium, Campylobacter, Staphylococcus, Streptococcus*, and *E. coli* bacterium. Further examples of pathogens include *Salmonella typhimurium, Salmonella infantis, Salmonella* Hadar, *Salmonella enteritidis, Salmonella* Newport, *Salmonella* Kentucky, *Clostridium perfringens, Staphylococcus aureus, Streptococcus uberis, Streptococcus suis, Escherichia coli, Campylobacter jejuni*, and *Fusobacterium necrophorum*.

As used herein a viral pathogen includes an infectious respiratory virus. Infectious respiratory viruses relevant to different animals are known and recognized in the art. Chickens (or poultry) are susceptible to respiratory viruses including Newcastle disease virus (NDV), avian influenza virus, infectious bronchitis virus (avian coronavirus), infectious laryngotracheitis virus, avian pneumovirus, adenoviruses, reoviruses. Swine (or pigs) are susceptible to porcine reproductive an respiratory syndrome virus (PRRSV), swine influenza virus (SIV), pseudorabies virus (PRV), as well as porcine respiratory coronavirus (PRCV), porcine cytomegalovirus (PCMV), porcine paramyxovirus (PPMV), hemagglutinating encephalomyelitis virus (HEV), encephalomyocarditis virus, porcine parvovirus, porcine adenovirus, porcine enterovirus. Cattle are susceptible to type I bovine herpesvirus (infectious bovine rhinotracheitis virus), parainfluenzavirus Type 3, bovine respiratory syncytial virus (BRSV), bovine viral diarrhea virus (BVDV), bovine adenovirus, bovine coronavirus. Humans are susceptible to respiratory syncytial virus (RSV), parainfluenza viruses, adenoviruses, influenza viruses, human coronaviruses (such as SARSCoV and the recent SARSCoV-2 (COVID-19)).

The compositions may be administered orally, parentally, nasally, or mucosally. Parental administration includes subcutaneous, intramuscular and intravenous administration.

In some aspects, administration includes feeding the poultry, or spraying onto the poultry. In other aspects, administration includes on ovo administration or in ovo administration. In an embodiment, administered comprises in ovo administration. In an embodiment, administered comprises spray administration. In an embodiment, administered comprises immersion, intranasal, intramammary, topical, or inhalation.

In an embodiment, administered comprises administration of a vaccine. In an embodiment, the animal is administered a vaccine prior to the administration of the composition. In an embodiment, the animal is poultry and the poultry is administered a vaccine prior to the administration of the composition. In an embodiment, the animal is swine and the swine is administered a vaccine prior to the administration of the composition. In an embodiment, the animal is administered a vaccine concurrently with the administration of the composition. In an embodiment, the animal is poultry and the poultry is administered a vaccine concurrently with the administration of the composition. In an embodiment, the animal is poultry and the poultry is administered a vaccine, wherein said vaccine comprises a vaccine that aids in the prevention of coccidiosis. In an embodiment, the animal is swine and the swine is administered a vaccine concurrently with the administration of the composition.

In aspects the animal is vaccinated in conjunction with administration. The animal may be vaccinated prior to administration of the compositions disclosed herein. The animal may be vaccinated with an coccidiosis vaccine. Coccidiosis vaccines are known in the art, for example, COCCIVAC.

In some embodiments, administration is by way of injection or infusion. In one embodiment, the composition is administered to a cow by way of intra-mammary infusion.

In an embodiment of the method(s), the method does not comprise administration of an antibiotic.

In some embodiments, the compositions or combinations may additionally include one or more prebiotic. In some embodiments, the compositions may be administered along with or may be coadministered with one or more prebiotic. Prebiotics may include organic acids or non-digestible feed ingredients that are fermented in the lower gut and may serve to select for beneficial bacteria. Prebiotics may include mannan-oligosaccharides, fructo-oligosaccharides, galacto-oligosaccharides, chito-oligosaccharides, isomalto-oligosaccharides, pectic-oligosaccharides, xylo-oligosaccharides, and lactose-oligosaccharides.

The compositions may further include one or more component or additive. The one or more component or additive may be a component or additive to facilitate administration, for example by way of a stabilizer or vehicle, or by way of an additive to enable administration to an animal such as by any suitable administrative means, including in aerosol or spray form, in water, in feed or in an injectable form. Administration to an animal may be by any known or standard technique. These include oral ingestion, gastric intubation, or broncho-nasal spraying. The compositions disclosed herein may be administered by immersion, intranasal, intramammary, topical, mucosally, or inhalation. When the animal is a bird the treatment may be administered in ovo or by spray inhalation.

Compositions may include a carrier in which the bacterium or any such other components is suspended or dissolved. Such carrier(s) may be any solvent or solid or encapsulated in a material that is non-toxic to the inoculated animal and compatible with the organism. Suitable pharmaceutical carriers include liquid carriers, such as normal saline and other non-toxic salts at or near physiological concentrations, and solid carriers, such as talc or sucrose and which can also be incorporated into feed for farm animals. When used for administering via the bronchial tubes, the composition is preferably presented in the form of an aerosol. A dye may be added to the compositions hereof, including to facilitate chacking or confirming whether an animal has ingested or breathed in the composition.

When administering to animals, including farm animals, administration may include orally or by injection. Oral administration can include by bolus, tablet or paste, or as a powder or solution in feed or drinking water. The method of administration will often depend on the species being feed or administered, the numbers of animals being fed or administered, and other factors such as the handling facilities available and the risk of stress for the animal.

The dosages required will vary and need be an amount sufficient to induce an immune response or to effect a biological or phenotypic change or response expected or desired. Routine experimentation will establish the required amount. Increasing amounts or multiple dosages may be implemented and used as needed.

The strains disclosed herein demonstrate certain phenotypic properties. Without wishing to be bound by theory, it is believed that these phenotypic properties at least contribute to increasing animal health.

In some embodiments, the isolated strains secrete at least one of cyclic dipeptides (cyclo(his-phe) and cyclo (phe-pro), short chain fatty acids (2-hydroxy-3-methylvalerate and alpha-hydroxyisocaproate), betaine, dimethylglycine, essential amino acids (e.g., allo-threonine, phosphothreonine, histidine, lysine, phenylalanine, tryptophan, leucine, isoleucine, and cysteine s-sulfate), nucleotides (e.g., adenosine 5'-monophosphate (AMP), uridine 5'-monophosphate (UMP), cytidine 5'-monophosphate (5'-CMP), and cytidine 2'3'-cyclicmonophosphate), myo-inositol, and indolin-2-one. Some of the aforementioned molecules provide beneficial characteristics to the host, including increased weight, pro-inflammatory effects, and antibiotic effects.

In some embodiments, the composition including the isolated first *Lactobacillus reuteri* strain (strain 3632) and the isolated second *Lactobacillus reuteri* strain (strain 3630) in combination, will secrete certain beneficial molecules in larger quantities than when individually cultured. For example, with combinations and cocultures of strains 3630 and 3632, increased levels of each of the following are provided or secreted (as determined from culture supernatants): dimethylglycine, allo-threonine, 1-methyl-4-imidazoleacetate, 4-imidazoleacetate, lysine, N6-methyllysine, N6, N6-dimethyllysine, 5-aminovalerate, and tyrosine, 4-hydroxyphenylpyruvate, indolacetate, and gamma-glutamylglutamine, glucose 6-phosphate, 4-hydroxyl-2-oxoglutaric acid, and myo-inositol, Uridine 5'-monophosphate (UMP), Cytidine 5'-monophosphate (5'-CMP), 3'-5'-uridylyluridine, O-sulfo-L-tyrosine, indole 3 acetamide, indolin-2-one and daidzein. In particular, when the strains 3630 and 3632 are combined in cultures or are grown together, significant and synergistic amounts (more than just additive) of some beneficial molecules are present or secreted. In particular embodiments, significant amounts of the molecules 4-hydroxyphenylpyruvate and glucose 6-phosphate are secreted or present with combinations of strains 3630 and 3632, or with compositions including a mix of about equal amounts of strains 3630 and 3632.

In some embodiments, the animal administered the composition exhibits a shift in the microbiome content of the gastrointestinal tract. For example, there may be an increase in the amount of bacteroidaceae bacteria in the gut of an animal that has been administered the composition described herein, as compared to an animal that was not administered the composition.

In embodiments of the present invention, the composition includes a combination of two isolated *Lactobacillus reuteri* strains.

Without wishing to be bound by a particular theory, it is believed that the immunogenic probiotic composition of the present disclosure can stimulate a subject's immune response. In this regard, and in particular, the composition is believed to improve vaccine efficacy, and decrease viral load and/or increase viral titer of a subject that is infected with an infectious respiratory disease or that is administered a vaccine for an infectious respiratory virus.

In some embodiments, the immunogenic probiotic composition is administered in conjunction with an infectious respiratory disease vaccine. By way of example, the composition may be administered before, after, or concurrently (either separately or co-administration) with an infectious respiratory disease vaccine. The composition may be administered to a subject as part of a vaccination or treatment regimen for an infectious respiratory disease. The infectious respiratory disease vaccine may be a live attenuated vaccine, inactivated vaccine, or subunit vaccine. Subunit vaccines include a protein or glycoprotein components of a viral pathogen that are capable of inducing a protective immune response.

In a preferred embodiment, the immunogenic probiotic composition is administered to the subject orally and the vaccine is administered by inhalation or ocular route. In another preferred embodiment, the immunogenic probiotic composition is administered to the subject orally and the vaccine is administered parenterally.

Infectious respiratory disease includes coronavirus disease including avian coronavirus disease infectious bronchitis due to infectious bronchitis virus (IBV); porcine reproductive and respiratory syndrome (PRRS); influenza disease including avian influenza, canine influenza and swine influenza; parainfluenza disease, including canine parainfluenza and feline influenza; adenovirus disease including avian adenovirus, porcine adenovirus, bovine adenovirus. The infectious respiratory diseases also apply in corresponding instances to humans, including such as human coronavirus disease and COVID-19, influenza, respiratory syncytial virus disease, parainfluenza.

Examples of infectious respiratory disease vaccines include MILDVAC-ARK, MILDVAC-GA-98, MILDVAC-Ma5, a vaccine to control infectious bronchitis virus (IBV) (Merck (Intervet) Animal Health). This live virus vaccine is prepared from a cloned Ma5 strain of Massachusetts type bronchitis; PREVACENT PRRS vaccine, a modified live virus vaccine to control PRRS; and NOBIVAC Canin e Parainfluenza Vaccine (Merck (Intervet)).

Some infectious respiratory diseases may be caused by coronavirus, as in the case of IBV. Examples of human coronaviruses include SARS COV-2, SARS COV, MERS COV, 229E, NL63, OC43, and HKU1. A coronavirus vaccine may include a coronavirus viral protein. A coronavirus vaccine may be based on mRNA or otherwise. A coronavirus vaccine may be a live attenuated vaccine.

In some embodiments, the invention provides a method of stimulating an immune response in a subject by administering to the subject an immunogenic probiotic composition disclosed herein. The composition may be administered in conjunction with an infectious respiratory disease vaccine. The composition may be administered prior to an infectious respiratory disease vaccine. The composition may be administered prior to and in conjunction with an infectious respiratory disease vaccine. The composition may be administered in conjunction with an infectious respiratory disease vaccine and also after the vaccine is administered, such as for a period of days or week thereafter.

In some embodiments, the invention provides a method of stimulating an immune response in a subject by administering to the subject an immunogenic probiotic composition disclosed herein in conjunction with an infectious respiratory disease viral protein. An infectious respiratory disease viral protein is a protein encoded by the viral genome. In a preferred embodiment, the viral protein is a surface exposed viral protein.

The immune response may be measured by any method known in the art. Examples of measuring immune response include measuring antibody titer, cytokine profiling, and histopathology methods. Quantitative PCR may be utilized to measure immune response, circulating or shed virus, or viral response.

Cytokine profiling is typically done using ELISA using lung/tracheal/intestinal homogenates or serum samples. In the absence of reagents needed for ELISA (antibodies for detection of various cytokines) cytokine profiling is done using qRT-PCR on mRNA isolated from RNAlater preserved samples. For example, tissue samples can be collected in RNAlater for cytokine mRNA isolation and/or examination either qualitatively and/or quantitatively by qRT-PCR Commonly affected cytokines in COVID 19 disease include, but not limited to, IL-4, IL-6, IL-10, TNF-α, IFN-γ, CCL-17, and CCL-22.

Histopathology involves chemical fixation of tissues in buffered formalin, processing, sectioning, and staining with common stains like eosin and haemotoxylin and is typically done to capture the microscopical pathological changes in tissues caused by infectious respiratory disease, such as with coronavirus such as COVID-19 or with influenza. At a more granular level, histopathology can be used to examine parameters including qualitative and/or quantitative changes in immune cell populations, structural changes, edema, hemorrhage, etc. due to an infectious respiratory disease, including COVID-19 disease (or SARS-CoV-2 infection). Since around 60% of the COVID-19 patients have diarrhea, histopathology of gut associated lymphoid tissues, such as Peyer's patches allows examination of immune cell infiltration and inflammation.

In an embodiment, stimulating an immune response includes increasing the antibody titer of an antibody selective for a viral antigen. The antibody titer can be measured by way of ELISA, or another suitable method.

In a preferred embodiment, the immunogenic probiotic composition is administered to the subject orally and the vaccine is administered by inhalation (oculonasal route), oral route or parenterally. In a embodiment, the immunogenic probiotic composition is administered to the subject orally, such as through or in feed or food or in water such as in daily water administered to the animal, and the vaccine is administered by inhalation (oculonasal route), oral route or parenterally.

In one embodiment, the invention provides a method of vaccinating a subject for an infectious respiratory disease. The method includes administering the immunogenic probiotic composition described herein and an infectious respiratory disease vaccine to a subject.

In some embodiments, the invention provides a method of increasing antibody titer in a subject when the subject is exposed to an infectious respiratory disease. In some embodiments, the invention provides a method of increasing antibody titer in a subject when the subject is exposed to an infectious agent, particularly an infectious respiratory agent. The method includes administering an effective amount of the immunogenic probiotic composition described herein to a subject before or after exposure to an infectious respiratory disease or infectious disease agent. In one embodiment, the administration of a compound provided herein, particularly an immunogenic probiotic composition provided herein, to a subject having respiratory viral infection or exposed to a respiratory virus reduces peak viral load. In one embodiment, the administration of an immunogenic probiotic composition provided herein to a subject having respiratory viral infection reduces or inhibits viral replication. In one embodiment, the administration of an immunogenic probiotic composition provided herein to a subject having respiratory viral infection reduces or inhibits viral transmission. In one embodiment, the administration of a immunogenic probiotic composition provided herein to a subject having respiratory viral infection or exposed to a respiratory viral agent stimulates antibody production which is selective or specific for an infectious respiratory disease antigen or enhances or increases the amount of antibody selective for an infectious respiratory disease antigen. In an embodiment, the antibody is selective for an infectious respiratory disease antigen. In some embodiments, the composition is administered to the subject at the onset of symptoms of an infectious respiratory disease. In some embodiments, the immunogenic probiotic composition is administered in conjunction with an infectious respiratory disease vaccine. In some embodiments, the antibody titer is increased by at least 10%, at least 20%, at least 30%, at least 50%, or at least 75%, as compared to a subject that was not administered the immunogenic probiotic composition. In some embodiments, the infectious respiratory disease is a coronavirus, influenza virus, parainfluenza virus, adenovirus, respiratory syncytial virus, parvovirus, reovirus, paramyxovirus or viral diarrhea virus associated disease In some embodiments, the invention provides a method of decreasing viral load in a subject. The method includes administering an effective amount of the immunogenic probiotic composition described herein to a subject before or after exposure to an infectious respiratory disease. In one embodiment, the administration of an immunogenic composition described herein to a subject decreases peak viral load. In some embodiments, the composition is administered to the subject at the onset of symptoms of an infectious respiratory disease. In some embodiments, the immunogenic probiotic composition is administered in conjunction with an infectious respiratory disease vaccine. In some embodiments, the viral load is decreased by at least 10%, at least 20%, at least 30%, at least 50%, or at least 75%, as compared to a subject that was not administered the immunogenic probiotic composition.

In some embodiments, the invention provides a method of decreasing viral shedding in a subject. The method includes administering an effective amount of the immunogenic probiotic composition described herein to a subject before or after exposure to an infectious respiratory disease. In some embodiments, the composition is administered to the subject at the onset of symptoms of an infectious respiratory disease. In some embodiments, the immunogenic probiotic composition is administered in conjunction with an infectious respiratory disease vaccine. In some embodiments, the viral shedding is decreased by at least 10%, at least 20%, at least 30%, at least 50%, or at least 75%, as compared to a subject that was not administered the immunogenic probiotic composition.

Definitions

As used herein, "isolated" means that the subject isolate has been separated from at least one of the materials with which it is associated in a particular environment, for example, its natural environment.

Thus, an "isolate" does not exist in its naturally occurring environment; rather, it is through the various techniques known in the art that the microbe has been removed from its natural setting and placed into a non-naturally occurring state of existence. Thus, the isolated strain or isolated microbe may exist as, for example, a biologically pure culture in association with an acceptable carrier.

As used herein, "individual isolates" should be taken to mean a composition, or culture, comprising a predominance of a single species, or strain, of microorganism, following separation from one or more other microorganisms. The phrase should not be taken to indicate the extent to which the microorganism has been isolated or purified. However, "individual isolates" can include substantially only one species, or strain, of microorganism.

In certain aspects of the disclosure, the isolated *Lactobacillus reuteri* strain exist as isolated and biologically pure cultures. It will be appreciated by one of skill in the art, that an isolated and biologically pure culture of a particular *Lactobacillus reuteri* strain, denotes that said culture is substantially free (within scientific reason) of other living organisms and contains only the individual *Lactobacillus reuteri* strain in question. The culture can contain varying concentrations of said isolated *Lactobacillus reuteri* strain. The present disclosure notes that isolated and biologically pure microbes often necessarily differ from less pure or impure materials.

In some embodiments of the present invention, the composition includes a combination of two isolated *Lactobacillus reuteri* strains. In some embodiments of the present invention, the composition includes a combination of two or more isolated *Lactobacillus reuteri* strains.

As used herein, the term "bacterial consortia", "bacterial consortium", "microbial consortia", or "microbial consortium" refers to a subset of a microbial community of individual microbial species, or strains of a species, which can be described as carrying out a common function, or can be described as participating in, or leading to, or correlating with, a recognizable parameter, such as a phenotypic trait of interest (e.g. increasing vaccine efficacy). The community may comprise two or more species, or strains of a species (eg., *Lactobacillus reuteri* strains 3632 and 3630), of microbes. In some instances, the microbes coexist within the community symbiotically.

As used herein, the terms "colonize" and "colonization" include "temporarily colonize" and "temporary colonization".

As used herein, "probiotic" refers to a substantially pure microbe (i.e., a single isolate) or a mixture of desired microbes, and may also include any additional components (e.g., carrier) that can be administered to an animal to provide a beneficial health effect. Probiotics or microbial compositions of the invention may be administered with an agent or carrier to allow the microbes to survive the environment of the gastrointestinal tract, i.e., to resist low pH and to grow in the gastrointestinal environment.

As used herein, "carrier", "acceptable carrier", or "pharmaceutical carrier" are used interchangeably and refer to a diluent, adjuvant, excipient, or vehicle with which the compound is administered. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Handbook of Pharmaceutical Excipients, (Sheskey, Cook, and Cable) 2017, 8th edition, Pharmaceutical Press; Remington's Pharmaceutical Sciences, (Remington and Gennaro) 1990, 18th edition, Mack Publishing Company; Development and Formulation of Veterinary Dosage Forms (Hardee and Baggot), 1998, 2nd edition, CRC Press.

As used herein, "delivery" or "administration" means the act of providing a beneficial activity to a host. The delivery may be direct or indirect. An administration could be by an oral, ocular, nasal, inhalation, parenteral, or mucosal route. For example without limitation, an oral route may be an administration through drinking water, animal feed, or edible solid, a nasal route of administration may be through a spray or vapor, and a mucosal route of administration may be through direct contact with mucosal tissue. Mucosal tissue is a membrane rich in mucous glands such as those that line the inside surface of the nose, mouth, esophagus, trachea, lungs, stomach, gut, intestines, and anus. In the case of birds, administration may be in ovo, i.e. administration to a fertilized egg. In ovo administration can be via a liquid which is sprayed onto the egg shell surface, or an injected through the shell. Mucosal route of administration includes administration by inhalation of spray, aerosol, nebulized material, or vapor.

As used herein, the terms "treating", "to treat", or "treatment", include restraining, slowing, stopping, inhibiting, reducing, ameliorating, or reversing the progression or severity of an existing symptom, disorder, condition, or disease. A treatment may also be applied prophylactically to prevent or reduce the incidence, occurrence, risk, or severity of a clinical symptom, disorder, condition, or disease.

As used herein, "subject" includes bird, poultry, a human, or a non-human mammal. Specific examples include chickens, turkey, dogs, cats, cattle, and swine. The chicken may be a broiler chicken, egg-laying or egg-producing chicken. As used herein, the term "poultry" includes domestic fowl, such as chickens, turkeys, ducks, quail, and geese.

As used herein, "vaccine" refers to a composition that improves immunity to a particular disease. A vaccine typically contains an agent that resembles a disease-causing pathogen, and is often made from weakened or killed forms of the pathogen, its toxins or one of its surface proteins.

As used herein, the term "immunogenic" means than an agent is capable of eliciting an immune response, including an innate, humoral, or cellular immune response, and both. "Immunogenic" includes "immunomodulatory". An immunogenic composition is a composition that elicits an innate, humoral, or cellular immune response, or both.

As used herein, the term "immune response" includes a response by a subject that involves generation of antibodies that bind to an antigen (i.e., an antibody response). This does not exclude generation of a cell-mediated response.

The phrase "stimulating an immune response" includes a) generating an immune response against an antigen (e.g., a viral antigen) in a naïve individual; or b) increasing, reconstituting, boosting, or maintaining an immune response in an individual beyond what would occur if the composition was not administered. A composition is immunogenic if it is capable of attaining either of these criteria when administered in single or multiple doses.

As used herein "stimulating" an immune or immunological response refers to administration of a composition that initiates, boosts, modulates, or maintains the capacity for the host's immune system to react to a virus or antigen, at a level higher than would otherwise occur.

By "stimulating" is meant directly or indirectly increasing the level and/or functional activity of a target system (e.g., immune system). In certain embodiments, "stimulation" or "stimulating" means that a desired/selected response is more efficient (e.g., at least 10%, 20%, 30%, 40%, 50%, 60% or more), more rapid (e.g., at least 10%, 20%, 30%, 40%, 50%, 60% or more), greater in magnitude (e.g., at least 10%, 20%, 30%, 40%, 50%, 60% or more), and/or more easily induced (e.g., at least 10%, 20%, 30%, 40%, 50%, 60% or more) than if the vaccine had been used alone.

The term "adjuvant(s)" describes a substance, compound, agent or material useful for improving an immune response or immune cell or component stimulation, and may in some instances be combined with any particular antigen in an immunological, pharmaceutical or vaccine composition. Adjuvants can be used to increase the amount of antibody and effector T cells produced and to reduce the quantity of antigen or immune stimulant or modulator and the frequency of injection. Although some antigens are administered without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, California, p. 384). In a preferred aspect an adjuvant is physiologically and/or pharmaceutically acceptable in a mammal, particularly a human. The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., Eur. J Immunol. 9:363-366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390-398, 1981; and Hunter et al., J. Immunol. 127:1244-1250, 1981).

Any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment." In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

Throughout this specification, quantities are defined by ranges, and by lower and upper boundaries of ranges. Each lower boundary can be combined with each upper boundary to define a range. The lower and upper boundaries should each be taken as a separate element. Two lower boundaries or two upper boundaries may be combined to define a range.

Deposit Information

*Lactobacillus reuteri* strain "3630" was deposited on 19 Jun. 2020 according to the Budapest Treaty in the American Type Culture Collection (ATCC), ATCC Patent Depository, 10801 University Boulevard, Manassas, Va., 20110, USA. The deposit has been assigned ATCC Patent Deposit Number PTA-126787.

*Lactobacillus reuteri* strain "3632" was deposited on 19 Jun. 2020 according to the Budapest Treaty in the American Type Culture Collection (ATCC), ATCC Patent Depository, 10801 University Boulevard, Manassas, Va., 20110, USA. The deposit has been assigned ATCC Patent Deposit Number PTA-126788.

Access to the deposits is available during the pendency of this application to persons determined by the Commissioner of Patents and Trademarks to be entitled thereto under 37 C.F.R. § 1.14 and 35 U.S.C. § 122. Upon allowance of any embodiments in this application, all restrictions on the availability to the public of the variety is irrevocably removed.

The deposits is maintained in the ATCC depository, which is a public depository, for a period of 30 years, or 5 years after the most recent request, or for the effective life of the patent, whichever is longer, and is replaced if a deposit becomes nonviable during that period.

The present disclosure may be better understood with reference to the examples, set forth below. The following examples are put forth so as to provide those of ordinary skill in the art with a complete disclosure and description of how the compounds, compositions, and/or methods claimed herein are made and evaluated, and are intended to be purely exemplary and are not intended to limit the disclosure. It is appreciated that other embodiments and uses is apparent to those skilled in the art and that the invention is not limited to these specific illustrative examples or preferred embodiments.

Example 1

Isolation and Characterization of *L. reuteri* 3630 and 3632

*L. reuteri* 3630 and 3632 were isolated from chicken cecum. Morphology of these strains include opaque, circular colonies with slight whitish center. The LR 3630 colonies have whitish pigmentation and the LR 3632 colonies include dull orange pigmentation. These strains are non-spore forming The strains are sequenced by PacBio sequencing. 3632 contained 7 contigs and yield a total estimated genome size of 2.4 Mb and LR 3630 contained 5 contigs yielding an estimated genome size of 2.4 Mb. Phylogenetic relationships of the genomes are explored with UBCG v3.0 using default settings. This software tool employs a set of 92 single-copy core genes commonly present in all bacterial genomes. These genes then are aligned and concatenated within UBCG using default parameters. The estimation of robustness of the nodes is done through the gene support index (GSI), defined as the number of individual gene trees, out of the total genes used, that present the same node. A maximum-likelihood phylogenetic tree is inferred using FastTree v.2.1.10 with the GTR+CAT model. LR strains 3632 and 3630 isolates show closest relationship to *L. reuteri.*

Example 2

Effect of Probiotics on Infectious Bronchitis Vaccine Serology

The effect of probiotics on Infectious Bronchitis Vaccine serology is tested. Chickens are divided into thirteen test groups, each group having 14 birds. See Table 1 for test groups and relevant treatments.

TABLE 1

| Group ID | Number of Chickens Enrolled | Vaccination/Probiotic Treatment(s) | Vaccination/ Probiotic Route | Challenge (26 DOA*** ) | Challenge Volume/Route | Necropsy (31 DOA*** ) |
|---|---|---|---|---|---|---|
| 1 | 14 | None | NA | None | N/A | 5 days post challenge |
| 2 | 14 | None/LR3632 | NA/DW* | None | N/A | |
| 3 | 14 | None/LR3630 | NA/DW* | None | N/A | |
| 4 | 14 | None | NA | IBV M41 | 60 μL total or 30 μL per eye/Ocular | |
| 5 | 14 | None/LR3632 | NA/DW* | IBV M41 | 60 μL total or 30 μL per eye/Ocular | |
| 6 | 14 | None/LR3632 and LR3630 | NA/Spray** | IBV M41 | 60 μL total or 30 μL per eye/Ocular | |
| 7 | 14 | None/LR3632 and LR3630 | NA/DW* | IBV M41 | 60 μL total or 30 μL per eye/Ocular | |
| 8 | 14 | IBV/LR3632 and LR3630 | Spray/DW* | IBV M41 | 60 μL total or 30 μL per eye/Ocular | |
| 9 | 14 | IBV/None | Spray/NA | IBV M41 | 60 μL total or 30 μL per eye/Ocular | |
| 10 | 14 | IBV/None | Spray/NA | None | N/A | |
| 11 | 14 | None/*Bacillus* | NA/DW* | IBV M41 | 60 μL total or 30 μL per eye/Ocular | |
| 12 | 14 | IBV/*Bacillus* | Spray/DW* | IBV M41 | 60 μL total or 30 μL per eye/Ocular | |
| 13 | 14 | None/*Bacillus* | NA/DW* | None | N/A | |

NA—not applicable;
DW—drinking water;
*SD 0-SD 26
**SD 0
*** day of age

At 24±2 days of age, blood drawn for serological testing.

Chickens in treatment groups 4, 5, 6, 7, 8, 9, 11, and 12 are challenged with IBV Mass at approximately 4 weeks of age by the ocular route (60 μL per chicken or 30 μL/eye).

After challenge a health observation is performed every day until necropsy at 5 days post challenge.

At SD 26±2 (day of challenge) to SD31±2 (day of necropsy), chickens in groups 1, 4, 5, 6, 7, 8, 9, 10, 11, and 12 have daily cloacal swabs taken for PCR.

Five days post challenge (SD31±2), chickens are euthanized and necropsied:

Examine lung from all chickens from groups 1-13 for gross lesions and record.

Examine trachea from all chickens from groups 1-13 for gross lesions and record.

Collect tracheal swabs from chickens in group 1-13 for IBV testing by PCR.

Dissect trachea from each chicken in groups 1, 4, 7 and 11. Place in a tube of 1.0 mL PBS, rock tube back and forth at least 5 times, remove trachea and retain PBS for sampling.

Collect ~2 cm section of trachea from each birds in groups 1-13 in buffered formalin for histology.

Collect approximately a dime size of lung tissue in a cryotube from each bird in groups 1, 4, 7 and 11. Store at −60° C. or below for microbiome analysis.

Collect approximately a dime size of lung tissue in formalin for all groups (1-13) for histology.

Collect contents of left cecum in a cryotube from each bird in groups 1, 4, 7, and 11. Place on ice packs or dry ice until stored long term at −60° C. or below for microbiome analysis.

Dissect right cecal tonsil from all birds in groups 1-13, cut the tissue in two pieces (longitudinally); transfer one piece to buffered formalin for histology and another piece to a another tube stored at −60° C. or below for IBV testing by PCR or other in vitro analysis.

Group 1—Birds in group 1 serve as no-treatment/non-challenge control and receive clean water during SD 0 to SD 26±2.

Group 2 and 5: Birds in group 2 and 5 receive *Lactobacillus reuteri* 3632 (Lot #20200424-LBRT3632.01-GF) via drinking water during SD 0 to 26±2. The probiotic is in the form as a lyophilized cake and each vial contains 200 doses. Each vial is Q.S.'d (quantum sufficit) to 100 ml with clean drinking water for 2 doses/mL dilution and volume is calculated of probiotic added to the bell waterer during the each probiotic treatment day and documented on a Probiotic Treatment Preparation form. For example, for 14 chickens: Need 14 chickens doses÷2 doses/mL=7.0 mL diluted probiotic.

Group 3: Birds in group 3 receive *Lactobacillus reuteri* 3630 (Lot #202000421-LBRT3630.01-GF) via drinking water during SD 0 to 26±2. The probiotic is available as lyophilized cake and each vial contains 200 doses. Each vial is diluted with 100 mL with clean drinking water for 2 doses/mL dilution and volume is calculated of probiotic added to the bell waterer during the each probiotic treatment day.

Group 4: Birds in group 4 serve as no-treatment/challenge controls. Birds receive clean water during SD 0 to SD 31±2.

Group 6: Birds in group 6 receive *Lactobacillus reuteri* 3632 (Lot #20200424-LBRT3632.01-GF) and *Lactobacillus reuteri* 3630 (Lot #202000421-LBRT3630.01-GF) via spray on SD 0. The probiotic is available as lyophilized cake and each vial contains 400 doses. Each vial is diluted with 28.0 mL of clean drinking water and mixed, 28.0 mL from each diluted vial of probiotic is combined (extra volume is used to prime the spray cabinet at approximately 40 mL). The spray cabinet administers 14.0 mL total to the cabinet for 100 birds. Birds are confined to the appropriate space (approximately 14%) when the probiotics are administered via commercial spray cabinet at 140 L/chicken.

Group 7: Birds in group 7 receive *Lactobacillus reuteri* 3632 (Lot #20200424-LBRT3632.01-GF) and *Lactobacillus reuteri* 3630 (Lot #202000421-LBRT3630.01-GF) via drinking water during SD 0 to 26±2. The probiotic is available as lyophilized cake and each vial contains 400 doses. Each vial is Q.S.'d (quantum sufficit) to 100 ml with clean drinking water for 4 doses/mL dilution and volume is calculated of probiotic added to the bell waterer during the each probiotic treatment day and documented on a Probiotic Treatment Preparation form.

Group 8: Birds in group 8 receive IBV vaccine via coarse spray route on SD 0 along with *Lactobacillus reuteri* 3632 (Lot #20200424-LBRT3632.01-GF) and *Lactobacillus* The probiotic is available as lyophilized cake and each vial contains 400 doses. Each vial is Q.S.'d (quantum sufficit) to 100 ml with clean drinking water for 4 dose/mL dilution and volume is be calculated of probiotic added to the bell waterer during the each probiotic treatment day and documented on a Probiotic Treatment Preparation form. The bulk re-hydrated probiotic can be used for all groups for that probiotic's water treatment.

Group 9 and 10: Birds in groups 9 and 10 receive IBV vaccine via coarse spray route on SD 0. Vaccine is administered according to manufacturer's instructions.

Group 11 and 13: Birds in group 11 and 13 receive *Bacillus amyloliquefaciens* spores (Lot #20200511-BAML.01GF) via drinking water during SD 0 to 26±2. The probiotic is available as lyophilized cake and each vial contains 200 doses. Each vial is diluted with 100.0 mL of clean drinking water for 2.0 doses/mL. From the re-hydrated probiotic, 0.5 mL/chicken is added to the bell waterer during each probiotic treatment day.

Group 12: Birds in group 12 receive IBV vaccine via coarse spray route on SD 0 and *Bacillus amyloliquefaciens* spores (Lot #20200511-BAML.01GF) via drinking water during SD 0 to 26±2.

The probiotic is available as lyophilized cake and each vial contains 200 doses. Each vial is Q.S.'d with clean drinking water to 100 mL for 2 doses/mL. From the re-hydrated probiotic, 0.5 mL/chicken is added to the bell waterer during each probiotic treatment day.

The birds are challenged with Avian Infectious Bronchitis Virus (IBV) Mass 41 strain. The titer is 6.70 log 10 EID50/mL and the dosage is 4.0 log 10 EID50/mL, 60 μL/bird, Ocular.

On SD 26±2, at 4-weeks-of-age, each bird from treatment groups 4, 5, 6, 7, 8, 9, 11, and 12 is challenged with 60 μL per bird (30 μL per eye) of IBV M41 challenge virus. Challenge is administered using a micropipette with sterile tip.

Chickens are observed daily post-challenge until necropsy (SD 27±2 through SD31±2). Clinical signs of IBV may include: coughing, sneezing, tracheal rales, depression, ruffled feathers, inappetence, huddling, wet or watery feces, and reluctance to move/rise.

On SD 24±2 (1-2 days before challenge), approximately 1-2 mL of blood samples are collected from the brachial vein using a 20-25 gauge needle and appropriately sized syringe. Blood is transferred to a serum tube or serum separator tube and allowed to coagulate.

Trachea and lung from each bird is evaluated on SD 33±2 at necropsy for gross lesion, and scored as normal or abnormal (serous, catarrhal or caseous exudates present in the trachea and congestion (pneumonia) in the lungs).

Cloacal swabs are collected from each bird in treatment groups 1, 4, 5, 6, 7, 8, 9, 10, 11, and 12 from SD 26±2 (day of challenge) to SD31±2 (day of necropsy).

Tracheal swabs are collected from each bird from groups 1-13 at 5 days post challenge at necropsy (SD31±2).

Dissect trachea from each bird in groups 1, 4, 7 and 11 and place in a cryotube with 1.0 mL of PBS (phosphate buffered saline), rock the vial back and forth at least 5 times and retain the rinse in a cryotube and store at −60° C. or below for microbiome analysis. The trachea can be removed and used for further sampling for histopathology.

Lung samples and tracheal samples are tested for microbiome data analysis.

Approximately a dime size piece of lung tissue and approximately 2 cm long section of trachea is collected from each bird from treatment groups 1-13 on SD 31±2 in buffered formalin.

Right cecal tonsil, secondary lymphoid tissue located at the cecal-rectal junction. Dissect ~2 cm long cecal-rectal junction is collected on SD 31±2. Each sample is cut into two pieces longitudinally (contents may be gently removed), one piece is stored in cryotubes for PCR testing (or other in vitro analysis) and another piece is stored in buffered formalin.

Antibody titer is measured from blood samples collected on study day 24. Antibody titer results are depicted in FIG. 1. Study group 8 (administered strains LR3632 and LR3630) shows approximately 20% increase in antibody titer as compared to chickens that were not administered strains 3632 and 3630.

Tracheal virus load and viral shedding (D0, D1, D2, D3, D4, and D5) are tested with varying amount of at least one of 3630, 3632, and vaccine.

Example 3

Antiviral Effect of *L. reuteri* on Porcine Reproductive and Respiratory Syndrome (PRRSV)

The effect of LR cells and LR supernatant (3630 and 3632) are tested on MARC-145 (Monkey Kidney) cells in a prevention and therapeutic context, in connection with PRRSV. Virus: GFP-PRRSV, MOI of 1.0; Bacteria: Stock ($10^6$ cells/mL).

MARC-145 cells are prepared 2-3 days prior to study. The cells are treated with undiluted and 2-fold serially diluted Bacteria/extract up to 1:32 (1:64) before or after PRRSV infection. In a prevention context, *Lactobacillus* cells or culture supernatant are added first and virus is added 2-4 hrs later. In a therapeutic context, virus is added first and *Lactobacillus* cells or culture supernatant is added next, 10 min or 1 hr post infection. The PRRSV inhibitory effect is analyzed by GFP expression and CPE up to 72 hours post infection (hpi).

Figure 2:
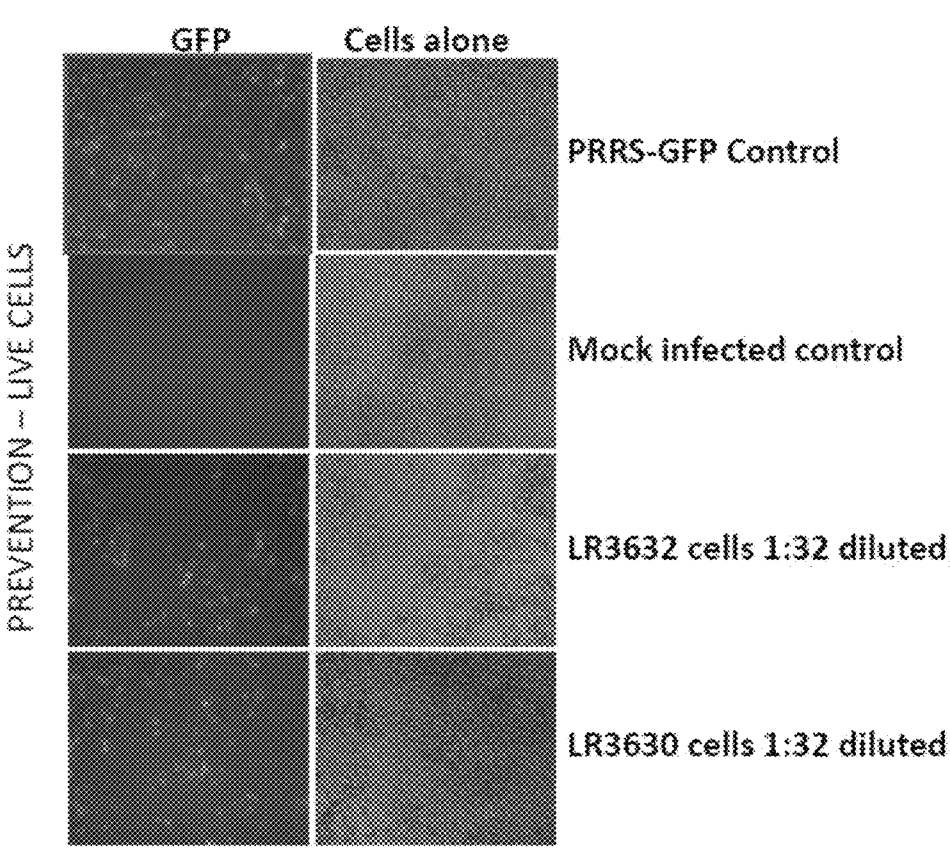
FIG. 2 depicts the effect of *Lactobacillus reuteri* cells on MARC-145 cells in preventing PRRSV infection.
Figure 3:
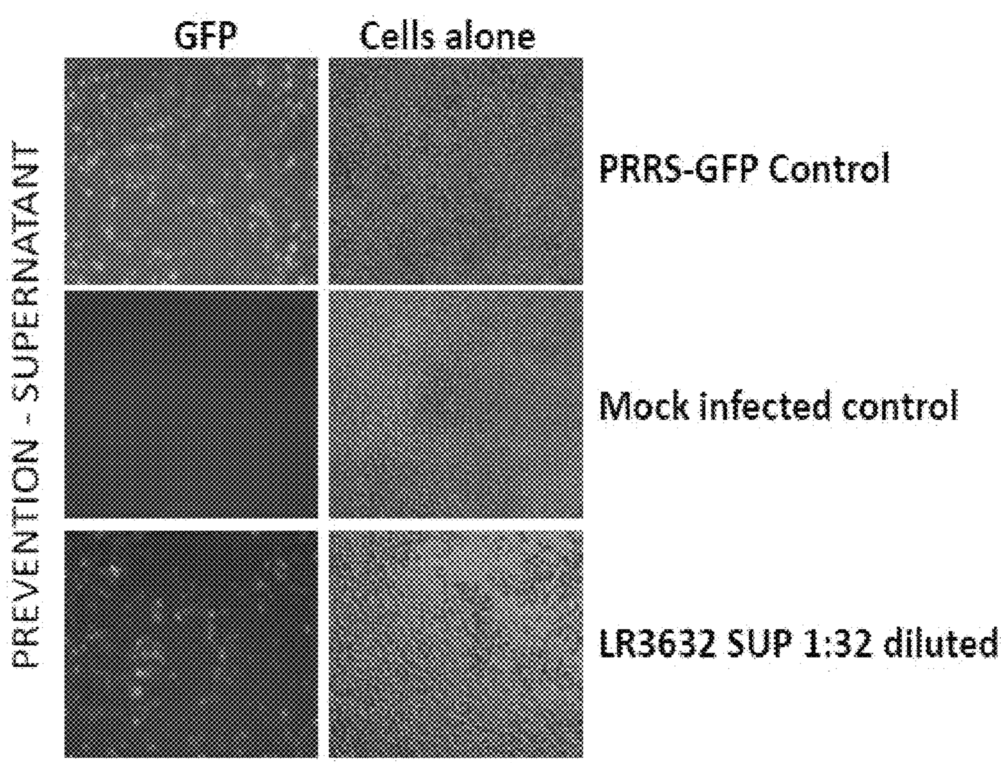
FIG. 3 depicts the effect of *Lactobacillus reuteri* supernatant on MARC-145 cells in preventing PRRSV infection.
Figure 4:
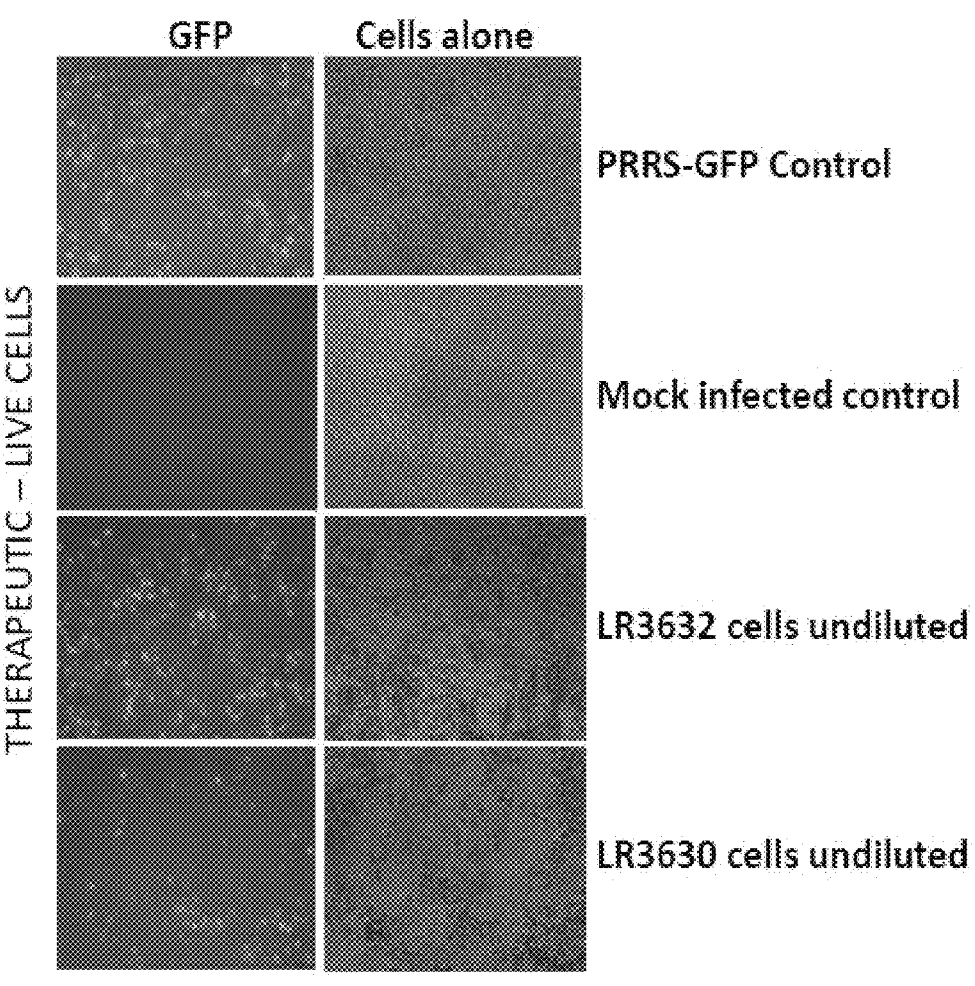
FIG. 4 depicts the effect of *Lactobacillus reuteri* cells on MARC-145 cells in treating PRRSV infection.
Figure 5:
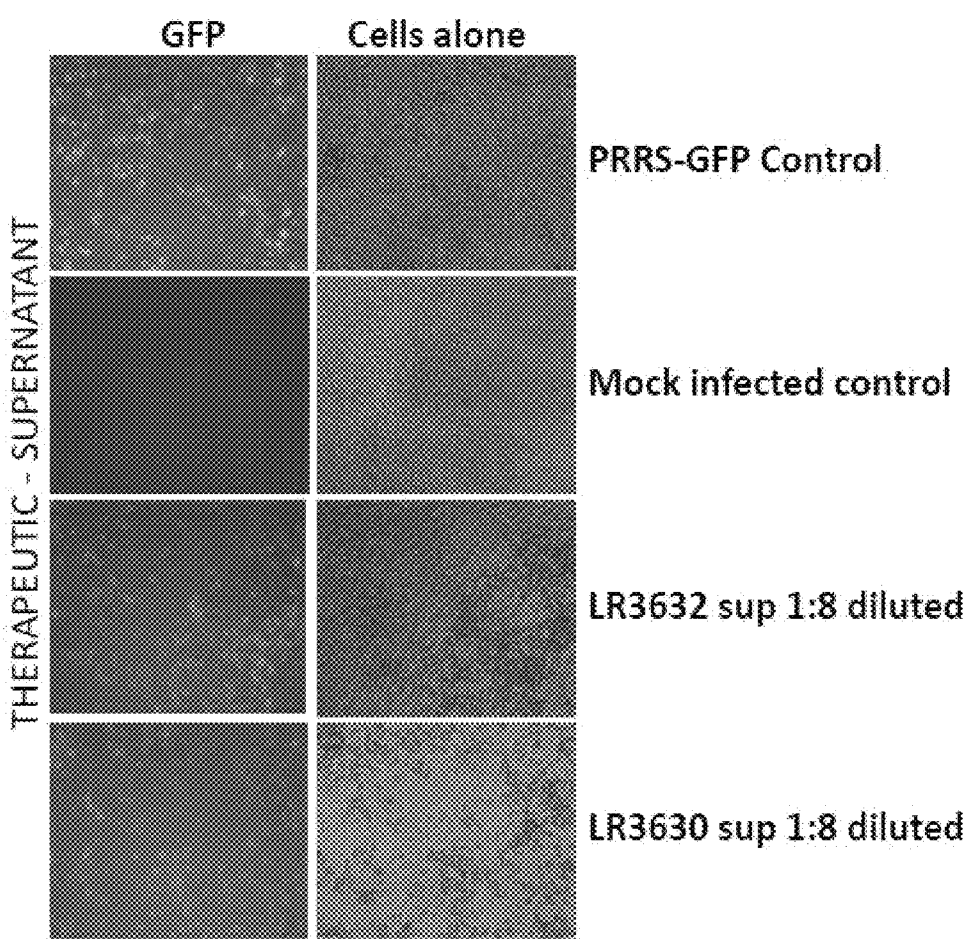
FIG. 5 depicts the effect of *Lactobacillus reuteri* supernatant on MARC-145 cells in treatment of PRRSV infection.

Live *Lactobacillus reuteri* strain 3632 or strain 3630 cells show more than 50% inhibitory effect on PRRSV at 1:16 to 1:32 dilutions in prevention setting. See FIG. 2. Similar inhibition (30-40%) was shown for both *Lactobacillus reuteri* supernatants in prevention setting. See FIG. 3. *Lactobacillus reuteri* strain 3632 and strain 3630 live cells somewhat inhibited PRRSV but both supernatants more efficiently inhibited virus replication in therapeutic setting. See FIGS. 4 and 5.

The efficacy of a PRRSV vaccine in combination with strains 3630 and 3632 is evaluated in growing swine following heterologous challenge with a virulent PRRS virus. The efficacy of vaccine in combination with *L. reuteri* strains 3630 and 3632 is based on the effectiveness of the vaccine to reduce lung lesions and viremia compared to a vaccinated control where 3630 and 3632 are not administered.

Blood samples for determination of PRRSV viremia are collected on Days 0 and 35. Nasal swabs to assess viral load are collected on Days 0 and 35. A body weight measurement (lbs) is taken on Day 0 and prior to the challenge on Day 35.

On Day 35, a 2 mL challenge dose is administered intranasally, with approximately 1 mL per nostril. The post-challenge phase is from Day 35 to Day 49. All pigs are individually assessed for depression, body condition and respiratory distress on Days 35-49 and scored for each clinical sign. Blood samples for PRRSV serum antibody determination (FFN) are collected on Days 42 and 49. Blood samples for determination of PRRSV viremia are collected on Days 38, 42, 45, and 49. Nasal swabs to assess viral load are collected on Days 38, 42, 45, and 49. A body weight measurement is obtained at the time of necropsy on Day 49. On Day 49, animals are humanely euthanized and lungs are scored by the Study Investigator who was blinded to treatment. Each of the seven pulmonary lobes is examined both visually and by palpation for gross characteristic lesions attributed to PRRSV. The amount of lesion/consolidation in each pulmonary lobe is scored as an actual between 0 and 100% of the lobe. The score for each lobe is entered into a weighted formula to calculate the percentage of lung with lesions.

Antibody titer is measured from blood samples collected on study day 24. Viral shedding is tested.

Example 4

Clinical Outcome and Virus Shedding in a Hamster SARS-CoV-2 Challenge Model

The effect of LR 3630 and LR 3632 are tested in a hamster SARS-CoV-2 challenge model. Male golden Syrian hamsters 5-7 weeks of age are tested in a 13 day study. On SD −7 to SD −1 and SD 1 to SD 4, hamsters in TG03, TG04, and TG05 receive appropriate dose of probiotic (see Table 2) via oral gavage once daily. On SD 0, all animals in TG02, TG03, TG04, and TG05 are be challenged via intranasal route with SARS-CoV-2 at a concentration of 105 TCID50 in 100 μL (50 μL per naris).

All animals are observed once per day and clinical scores are recorded.

Fecal swabs are collected daily from Days −1 to Day 5. Blood samples are collected on Days −7, −2, 1, 3, and 5. The blood volume collected in a week from an individual animal do not exceed 0.5 mL. At time of necropsy, larger volumes of blood are collected. All animals are be euthanized, and samples is collected for in vitro analysis.

TABLE 2

| Treatment Groups | | | | | |
|---|---|---|---|---|---|
| Group | Compound/Dose | Treatment Route/ Frequency | Dose of SARS-Cov-2 | Challenge Route | Number of Animals per Group |
| TG01 | No treatment (held in a separate room) | Not applicable (N/A) | No challenge | N/A | 7 |
| TG02 | No treatment | Not applicable | $10^5$ $TCID_{50}$ | IN (50 μL per nare) | 7 |

TABLE 2-continued

| Treatment Groups | | | | | |
|---|---|---|---|---|---|
| Group | Compound/Dose | Treatment Route/ Frequency | Dose of SARS-Cov-2 | Challenge Route | Number of Animals per Group |
| TG03 | *L. reuteri** ($10^7$ CFU/animal/day) | ***Gavage/ daily study Day −7 to 5 | on SD0 | IN (50 μL per nare) | 7 |
| TG04 | *L. reuteri*** ($10^5$ CFU/animal/day) | ***Gavage/ daily study Day −7 to 5 | | IN (50 μL per nare) | 7 |
| TG05 | *B. amyloliquefaciens* ($10^7$ CFU/animal/day) | ***Gavage/ daily study Day −7 to 5 | | IN (50 μL per nare) | 7 |

CFU-colony forming unit;
IN-intransal;
SD-Study day;
*each dose contains $5 \times 10^6$ CFU of *L.reuteri* strain 3630 in 0.25 mL and $5 \times 10^6$ CFU of *L.reuteri* strain 3632 in 0.25 mL
**each dose contains $5 \times 10^4$ CFU of *L.reuteri* strain 3630 in 0.25 mL and $5 \times 10^4$ CFU of *L.reuteri* strain 3632 in 0.25 mL
***no probiotic treatment on SD 0 (challenge day)

TABLE 3

| Schedule of Study Events. | | | | | | | | | |
|---|---|---|---|---|---|---|---|---|---|
| Day | Treat groups 3-5 (oral or gavage) | Challenge | Fecal swabs | Euthanize & sample including group 1 | Blood samples | Nasal Washes | Wt. | Clinical scoring | FECAL Appear-ance |
| −14 to −8 | | | | | | | | | |
| −7 | X | | | | X | | X | X | |
| −6 | X | | | | | | | X | |
| −5 | X | | | | | | | X | |
| −4 | X | | | | | | X | X | |
| −3 | X | | | | | | | X | |
| −2 | X | | | | X | X | | X | |
| −1 | X | | X | | | | X | X | |
| 0 | | X | X | | | | X | X | X |
| 1 | X | | X | | X | X | X | X | X |
| 2 | X | | X | | | | X | X | X |
| 3 | X | | X | | X | X | X | X | X |
| 4 | X | | X | X | X | X | X | X | X |
| 5 | | | X | X | X | X | X | X | X |

Challenge Virus:
SARS-CoV-2/Canada/ON/VIDO-01/2020/Vero'76/p.2 (Seq. available at GISAID—EPI-ISL-413015)
Titer:
$1\times10^5$~ TCID50 100 μL dose
Dosage/Volume/Route:
$1\times10^5$ TCID50/100 μL dose/IN

TABLE 4

| Formulations | |
|---|---|
| *Lactobacillus reuteri* 3632 | |
| Appearance | Lyophilized cake |
| Antigen composition | *Lactobacillus reuteri* 3632 |
| Dosage/Volume/Route | TG03 - $5 \times 10^6$ CFU/0.25 mL oral gavage<br>TG04 - $5 \times 10^4$ CFU/0.25 mL oral gavage |
| *Lactobacillus reuteri* 3630 | |
| Appearance | Lyophilized cake |
| Antigen composition | *Lactobacillus reuteri* 3630 |
| Dosage/Volume/Route | TG03 - $5 \times 10^6$ CFU/0.25 mL oral gavage<br>TG04 - $5 \times 10^4$ CFU/0.25 mL oral gavage |

TABLE 4-continued

| Formulations | |
|---|---|
| *Bacillus amyloliquefaciens* | |
| Appearance | Lyophilized cake |
| Antigen composition | *B. amyloliquefaciens* |
| Dosage/Volume/Route | TG05 - $10^7$ CFU/0.5 ml/oral gavage |

On the morning of SD 0, all animals in groups TG02, 03, 04, and 05 are challenged. TG01 is not challenged.

TABLE 5

| Clinical scores are measured as follows. | |
|---|---|
| Weight Score | |
| 0 | weight gain, or loss 0-4.9% |
| 1 | 5 to 14.9% loss |
| 2 | at to 24.9% loss |
| 3 | greater than 25% loss |

TABLE 5-continued

| Clinical scores are measured as follows. | |
|---|---|
| Nasal Signs | |
| 0 | no symptoms |
| 1 | discharge on external nares |
| 2 | nasal rattling or sneezing |
| 3 | mouth breathing |
| Activity Level | |
| 0 | fully playful |
| 1 | responds to play but does not initiate play |
| 2 | alert but not playful |
| 3 | not playful, not alert |

Nasal washes are done by introducing 400 uL of sterile saline flushed into one naris while the runoff is collected directly into the collection tube from the other naris. A short nozzle teat infusion cannula attached to a 1 mL syringe is introduced into the naris in such a way that the naris is blocked by the diameter of the cannula, so the flush is forced to go into one nasal cavity and run out the other, rather than back flowing out.

Nasal washes are done on SD −2, 1, 3, and 5. The nasal washes are stored at −80° c. and is used for viral quantification by qRT-PCR and for cytokine analysis. Those samples that are positive for virus by qRT-PCR are used for virus isolation and titration (TCID50) by cell culture.

Blood samples are collected in EDTA on SD −7, −2, 1, 3, and 5. The blood volume collected in a week from an individual animal do not exceed 0.5 mL. unless that animal is being euthanized.

Blood samples, nasal wash, and full necropsy are done on all euthanized hamsters. Hamsters are deeply anesthetized with isoflurane for nasal wash as described above.

Samples of nasal turbinates and each lung lobe are collected for viral load, RNA, and histopathology. Lungs are weighed, photographed, and any pathology noted prior to collection of tissue.

Primary outcome determinants include body weight, clinical scores, virus titers, cytokine profile analysis, and histopathology.

Example 5

Clinical Outcome and Virus Shedding in a Hamster SARS-CoV-2 Challenge Model

The experimental conditions of Example 4 are duplicated with the additional step of administering a coronavirus viral protein (e.g., surface exposed protein) in conjunction with at least one of LR 3630 and LR 3632.

Example 6

Effect of Infectious Bronchitis Vaccine Dose and Probiotic Treatment on Protection Against Virulent Infectious Bronchitis in Specific Pathogen Free Chickens This study relates to the development and evaluation of probiotic products and probiotic vectored vaccines to 1) improve gut health, 2) address food borne diseases, 3) improve production traits, and 4) enhance immune responses to vaccines. The general objective of this study was to collect translational data to assist in improving general health and immune response to various vaccines in animals and humans.

Objectives of this study are to determine the influence of probiotics on immune response to sub-optimal doses of infectious bronchitis virus vaccine, and to determine the effect of probiotics on virulent infectious bronchitis challenge virus shedding in specific pathogen free chickens.

Prophylactic use of vaccines has greatly improved the animal welfare and production performance of animals. However general health status of the animal affects the immune response to various vaccines which indirectly influence the vaccine efficacy and/or duration of the protection.

Infectious bronchitis virus (IBV) vaccine is one of the most commonly used vaccines to prevent infectious bronchitis disease in chickens. Infectious bronchitis virus is an avian coronavirus. In general, most of the IBV vaccines are effective against homologous IBV virus induced disease but provide limited or no protection against heterologous virulent IBV. Under commercial production conditions, due to subclinical infection and gut health issue, it is not uncommon to see unsatisfactory immune response to IBV vaccine.

It has been shown that the appropriate use of relevant probiotics improves the gut microbiome which leads to improvement in gut health. It has also been shown that certain metabolites of probiotics improve both local and systemic immune response, cellular and humoral immunity, and have anti-microbial activities. This study is designed to further evaluate the effect of probiotics on IBV vaccine efficacy and challenge virus shedding.

The schedule of events for this study are provided in Table 6.

TABLE 6

| Schedule of Events | | |
|---|---|---|
| Study Date (SD) | Chicken Age (Days) | Activity |
| 0 | 0 | Specific Pathogen Free (SPF) chickens (105) arrive at day of age. At arrival birds will be released, tagged in the neck, vaccinated and/or probiotic administration according to Table 7. Extra birds will be euthanized. |
| 7-10 | 7-10 | Birds will be tagged via wing web. |
| 1-28 ± 2 | 1-28 ± 2 | Daily administration of probiotics in drinking water to groups 2, 3, 4 and 5 |
| 0-28 ± 2* | 0-28 ± 2 | Weekly health observations. |
| 26 ± 2 | 26 ± 2 | Blood samples collected from all groups (1-9) |
| 28 ± 2 | 28 ± 2 | Challenge groups 1 through 9. |
| 29 ± 2-33 ± 2 | 29 ± 2-3 ± 2 | Daily health observations of all chickens. |
| 33 ± 2 | 33 ± 2 | Necropsy (must be 5 days post-challenge) of all remaining birds |

*Perform weekly health observations after release of acclimation.

The treatment groups for the study are provided in Table 7.

TABLE 7

Treatment Groups.

| Group ID | Number of Chickens Enrolled | Vaccination/ Probiotic Treatment(s) | Vaccination/ Probiotic Route | Challenge (28 ± 2 DOA) | Challenge Volume/ Route | Necropsy (33 ± 2 DOA) |
|---|---|---|---|---|---|---|
| 1 | 10 | None | NA | IBV M41 | 60 μL total or 30 μL per eye/Ocular | 5 days post challenge |
| 2 | 10 | IBV at 3.8 $EID_{50}$/LR3632 + L R3630 | Spray/DW* | IBV M41 | 60 μL total or 30 μL per eye/Ocular | |
| 3 | 10 | IBV at 2.8 $EID_{50}$/LR3632 + L R3630 | Spray/DW* | IBV M41 | 60 μL total or 30 μL per eye/Ocular | |
| 4 | 10 | IBV at 1.8 $EID_{50}$/ LR3632 + LR3630 | Spray/DW* | IBV M41 | 60 μL total or 30 μL per eye/Ocular | |
| 5 | 10 | IBV at 0.8 $EID_{50}$/LR3632 + L R3630 | Spray/DW* | IBV M41 | 60 μL total or 30 μL per eye/Ocular | |
| 6 | 10 | IBV at 3.8 $EID_{50}$/ None | Spray/NA | IBV M41 | 60 μL total or 30 μL per eye/Ocular | |
| 7 | 10 | IBV at 2.8 $EID_{50}$/None | Spray/NA | IBV M41 | 60 μL total or 30 μL per eye/Ocular | |
| 8 | 10 | IBV at 1.8 $EID_{50}$/ None | Spray/NA | IBV M41 | 60 μL total or 30 μL per eye/Ocular | |
| 9 | 10 | IBV at 0.8 $EID_{50}$/ None | Spray/NA | IBV M41 | 60 μL total or 30 μL per eye/Ocular | |

NA—not applicable;
DW—drinking water;
*SD0-SD28 ± 2

Study Design

- Housing space requirements for SPF chickens:
  - 0 to 6 weeks of age=83 sq inches (0.6 square feet)
  - Isolators contain 1152 square inches of space.
  - Each isolator can hold 14 chicks until 6 weeks of age.
- A total of 105 (90 for enrollment and 15 extras) Specific Pathogen Free (SPF) chickens arrive at day of age (DOA) and the healthiest chicks will be distributed into nine treatment groups. Nine groups contain 10 birds per group (see Treatment Groups, Table 7). Remaining unused chickens are humanely euthanized. Discrepancies in chicken numbers are documented.
- On the day of arrival, birds are released from acclimation by site veterinarian and documented.
- After arrival and release for acclimation, birds were observed weekly until challenged then daily until the end of study and health observations were documented.
- Birds were vaccinated and/or treated with probiotics according to Table 7.
- Chickens are housed in isolators by group (one group per isolator).
- At 26±2 days of age, all chickens have blood drawn for serological testing.
- Chickens in treatment groups 1 through 9 were challenged with IBV Mass at 4 weeks of age by the ocular route (60 μL total chicken or 30 μL/eye).
- After challenge a health observation was performed every day until necropsy at 5 days post challenge.
- Five days post challenge (SD33±2), all surviving chickens are euthanized and necropsied:
  - Collect tracheal swabs from all surviving chickens in group 1-9 for IBV testing by PCR.
  - Dissect trachea from each chicken in groups 1-9. Place in a tube of 1.0 mL PBS, rock tube back and forth at least 5 times, remove trachea and retain PBS for microbiome sampling.
  - Collect ~2 cm section of trachea from each bird in groups 1-9 in buffered formalin for histology.

Animal Selection and Identification

Details on the animals for the study are provided in Table 8.

TABLE 8

Animal Selection and Identification

| | |
|---|---|
| Species: | *Gallus gallus* |
| Breed: | White Leghorn |
| Sex: | Mixed |
| Number of Animals: | 105 chickens (90 required and 15 extras for attrition). Discrepancies in chicken numbers are documented at arrival. |

TABLE 8-continued

| Animal Selection and Identification | |
|---|---|
| Age at arrival: | DOA |
| Source of the Animals: | Valo BioMedia |
| Animal Identification: | Chickens double tagged (neck tag on day of arrival and wing tag applied 7-10 days after arrival) |
| Immunological Status: | Specific Pathogen Free (SPF) |

Animal Management

Husbandry

All chickens were housed and cared for under the Guide for the Care and Use of Agricultural Animals in Research and Teaching and all local standard operating procedures Non-medicated feed was provided ad libitum. Poultry feed lot/batch numbers utilized within the duration of the study are recorded. Clean water is provided ad libitum. Feed and water containers are cleaned and replaced as needed.

The chickens are observed and cared for by animal care staff and observed daily for the first seven days and at least once weekly until challenge. After challenge, daily observations are conducted until time of necropsy. Observations are documented.

Any chicken exhibiting a health concern is noted accordingly. Birds found dead post-challenge are necropsied to determine the cause of death, samples are not required, but may be taken to determine the cause of death. Any chicken requiring veterinary attention is treated as deemed necessary and any treatment is documented.

Housing

Chickens are housed in isolators by group that are HEPA filtered in and out for containment. Environmental conditions are maintained and adjusted appropriately for their age, according to the Guide for the Care and Use of Agricultural Animals in Research and Teaching, 3rd Edition. Daily care and husbandry tasks are performed according to SOPs. Movements in primary housing due to facility, animal welfare, or study specific reasons after arrival are acceptable and are documented. Animal facilities are properly cleaned, disinfected, and set-up prior to animal arrival. Fogging of animal rooms prior to animal occupancy is completed per SOPs. Facility entry requirements and care order are maintained to minimize the risk of organism spread between groups and other site rooms/buildings.

Identification

Chickens have identification (ID) tags applied, each of the same number. One tag is applied to the skin at the back of the neck (at arrival) and the second tag is applied to the wing-web (7-10 days after arrival). If tag falls off and can be retrieved, they are re-applied. Identification completion will be documented.

Conditioning

Beak trimming may be required to mitigate pecking issues or negative behaviors. Trimming of the beaks is performed by a veterinarian or designee utilizing a hot blade beak trimmer (example: Lyon beak trimmer).

If mild pecking occurs (superficial), an anti-pecking spray or lotion is utilized to treat the affected area on the chicken. Mild pecking trauma may have first aid applied to areas of trauma. First aid treatments of Pick-No-More® or Blu Kote® are pre-approved. Treatment is documented.

Randomization Procedures

90 SPF chickens are identified by a wing and neck tag. Each chicken is tagged with a unique chicken identification (ID) number. Tag ID numbers are completely randomized and assigned to 9 treatment groups; 10 SPF chickens per treatment group (as outlined in Table 7). Treatment Groups are not randomized to housing unit as separation and care order needs to be maintained to prevent cross-contamination between groups. All randomizations are done Microsoft Excel®.

Blinding/Masking Method

Laboratory personnel (except Fort Dodge GO) involved with the testing of study samples are blinded from study treatment groups. All samples are labeled with the unique chicken ID but have no association to treatment.

Vaccination and Probiotic Treatment

Probiotic Information—the probiotic and strain information is detailed in Tables 9 (LR3630) and 10 (LR3632).

TABLE 9

| LR3630 | |
|---|---|
| Serial/Lot No: | 20200421-LBRT3630.01-GF |
| Appearance: | Lyophilized |
| Antigen composition: | *Lactobacillus reuteri* 3630 (10 doses/vial single probiotic) |
| Route/Volume: | Refer to Table 7 |
| Storage conditions: | 2-8° C. |

TABLE 10

| LR3632 | |
|---|---|
| Serial/Lot No: | 20200424-LBRT3632.01-GF |
| Appearance: | Lyophilized |
| Antigen composition: | *Lactobacillus reuteri* 3632 (20 doses/vial single probiotic) |
| Route/Volume: | Refer to Table 7 |
| Storage conditions: | 2-8° C. |

IBV Vaccine Information—the vaccine information is detailed in Table 11.

TABLE 11

| | |
|---|---|
| Serial/Lot No: | MILDVAC-Ma5 10,000 dose/vial (Merck (Intervet) Animal Health) |
| Appearance: | Lyophilized |
| Antigen composition: | IBV Mass. |
| Route/Volume: | Coarse Spray route: 70 μL/chicken (based on spray pattern in fixed area). |
| Storage conditions: | 2-8° C. |

Probiotic and Vaccine Preparation

Group 1—Birds in group 1 serve as no-treatment/challenge control and receive clean water during SD 0 to SD 33±2.

Group 2 through 5: Birds in group 2 through 5 receive various dilutions of IBV vaccine (3.8, 2.8, 1.8 and 0.8 $EID_{50}$/70 μL dose respectively) by coarse spray using a spray cabinet at day of age. $EID_{50}$ refers to the Egg (or Embryo) Infective Dose, or the amount of virus that will infect 50% of inoculated eggs. *Lactobacillus reuteri* 3632+3630 via drinking water during SD 0 to 28±2. The probiotic is made available as lyophilized cake and each vial contains 400 doses. Each vial (one of each probiotic) is Q.S.'d (quantum sufficit) to 100 ml with clean drinking water for 4 doses/mL (0.25 mL/bird/dose) dilution and volume is calculated of probiotic added to the bell waterer during the each probiotic treatment day and documented. The bulk re-hydrated probiotic can be used for all groups for that probiotic's water treatment.

Group 6 through 9: Birds in group 6 through 9 receive various dilutions of IBV vaccine (3.8, 2.8, 1.8 and 0.8 $EID_{50}$/70 μL dose respectively) by course spray using a spray cabinet at day of age.

All IVPs (probiotics) and IBV vaccine are carefully mixed periodically during use. All IVP and IBV vaccine administration are documented.

Vaccine and Probiotic Administration

Commercial vaccine is administered to DOA SPF chicks via coarse spray route and probiotic is administered via drinking water.

A commercial spray cabinet is utilized to administer vaccine to birds in treatment groups 2 through 9 by the coarse spray route: 70 μL per bird. Spray cabinet is designed for 100 birds vaccinated at 7.0 mL total (70 μL per bird), so birds are confined to approximately 20% (2 groups or 20 birds with corresponding vaccination rates) of the total area of the spray basket. After vaccination, birds are placed directly into the isolators with a heat lamp to encourage preening.

Drinking water administration of probiotics is administered daily from SD 0 to SD28±2 (day of challenge). Probiotics are prepared daily and placed into bell drinkers.

The IBV vaccine is carefully mixed periodically during use. All IVP (probiotics) and IBV vaccine administration is documented.

IBV Vaccine Titration

The IBV commercial vaccine is titrated in 9-day-old embryonated SPF eggs by the allantoic fluid inoculation method. On day of vaccination at least three replicates of 1:10 fold serial dilutions of the virus are performed. Each dilution is used to inoculate at least 6 eggs per dilution, 0.1 mL per egg. Eggs are candled at 24 hours post-inoculation to remove infertile and dead eggs. Eggs are candled 7 days post inoculation and the live/dead documented. On the $7^{th}$ day post-inoculation, eggs are euthanized by refrigeration (minimum of 2-4 hours) and then examined individually for signs of disease including stunting, curling, clubbed down, and urates. Titration results are calculated by Reed Muench method. Titration procedure will be documented and included in the SMF.

Challenge

Challenge Information—information on the avian infectious bronchitis virus strain is provided in Table 12.

TABLE 12

| Avian Infectious Bronchitis Virus M41 Strain | |
|---|---|
| Serial/Lot No: | 4073-023-24Mar2018 |
| Titer: | 6.70 $\log_{10}$ $EID_{50}$/mL |
| Appearance: | Straw yellow looking in color |
| Antigen composition: | Infectious Bronchitis Virus M41 strain |
| Dosage/Volume/Route: | 4.0 $\log_{10}$ $EID_{50}$/mL, 60 μL/bird, Ocular |
| Storage conditions: | −70° C. or colder |

Challenge Virus Preparation

On day of challenge, the IBV M41 challenge virus is thawed rapidly in a 37±2° C. water bath and diluted in Phosphate Buffered Saline (PBS) to the target dose of 4.0 $\log_{10}$ $EID_{50}$/mL. Preparation of challenge virus is documented appropriately. Following challenge preparation, the IBV M41 challenge virus is placed on wet ice for transport to the animal facilities.

Challenge Virus Titration

The IBV M41 challenge virus is titrated in 9-day-old embryonated SPF eggs by the allantoic fluid inoculation method. On day of challenge at least three replicates of 1:10 fold serial dilutions of the challenge virus are performed. Each dilution is used to inoculate at least 6 eggs per dilution, 0.1 mL per egg. Eggs are candled at 24 hours post-inoculation to remove infertile and dead eggs. Eggs are candled 7 days post inoculation and the live/dead documented. On the $7^{th}$ day post-inoculation, eggs are euthanized by refrigeration (minimum of 2-4 hours) and then examined individually for signs of disease including stunting, curling, clubbed down, and urates. Titration results are calculated by Reed Muench method. Titration procedure is documented.

Challenge Virus Administration

On SD 28±2, at 4-weeks-of-age, each bird from all treatment groups is challenged with 60 μL per bird (30 μL per eye) of IBV M41 challenge virus. Challenge is administered using a micropipette with sterile tip. Ocular inoculation is performed by trained individuals to ensure the challenge is completely absorbed into each eye. Challenge virus administration is documented.

Post Challenge Observations

Clinical staff (Veterinarians, Clinical Associates, Veterinary Technician or designee) observe chickens daily post-challenge until necropsy (SD 29±2 through SD33±2). Clinical signs of IBV may include: coughing, sneezing, tracheal rales, depression, ruffled feathers, inappetence, huddling, wet or watery feces, and reluctance to move/rise. If a chicken exhibits a health concern, it is noted. Pre-mortality examination findings are documented. Health concern evaluations are documented.

A veterinarian humanely euthanizes, if necessary, and necropsy the chicken to determine the cause. If clinical signs are present at necropsy, clinically relevant samples may be collected, submitted for testing or stored appropriately (frozen or in neutral buffered formalin). Necropsy and deposition of animals are documented.

Sample Collection, Processing, and Testing

Blood Samples

On SD 26±2 (1-2 days before challenge), approximately 1 mL of blood sample is collected from the brachial vein using a 20-25 gauge needle and appropriately sized syringe. Blood is transferred to a serum tube or serum separator tube and allowed to coagulate. All blood collection information is recorded.

Following coagulation, blood samples are centrifuged up to 3000×g for 10-20 minutes. Samples are processed and serum collected within 24 hours of blood collection. Serum samples collected from each bird is separated into at least two aliquots. One or more aliquots may contain 120 μL or greater of serum for sample testing and the remaining aliquots placed for long-term storage. Serum samples are stored at ≤−10° C. An aliquoted sample from each bird is sent for IBV ELISA (Enzyme Linked Immunosorbent Assay).

Tracheal Swabs

Tracheal swabs are collected from each bird from groups 1-9 at 5 days post challenge at necropsy (SD33±2). Following collection, swab samples are transferred to a collection tube containing 3 ml of PBS and frozen at or below −10° C. The IBV viral nucleotides are purified. PCR detection of IBV is completed.

Tracheal Washing for Microbiome Analysis

Dissect trachea from each bird and place in a cryotube with 1.0 mL of PBS (phosphate buffered saline), rock the vial back and forth at least 5 times and retain the rinse in a cryotube and store at −60° C. or below for microbiome analysis. The trachea is removed and used for further sampling for histopathology. Samples are documented and tested as needed.

Trachea for Histopathology

Approximately 2 cm long section of trachea are collected from each bird on SD 33±2 in buffered formalin. Samples are documented.

Adverse Events (AE)

An adverse event (includes all associated terms) is any observation in animals, whether or not considered to be product-related, that is unfavorable and unintended and occurs after the use of an investigational veterinary product. In a commercial poultry production setting and with previous experiences, the following health conditions are common and expected, as outlined below. For the purpose of this study, these types of events are considered non-serious adverse events until the incidence exceeds the thresholds listed in any Treatment Group administered an investigational product.

TABLE 13

Thresholds
Thresholds for SPF Chickens in General (expected occurrences)

| Condition | Incidence | Threshold |
|---|---|---|
| Early Mortality | 5-10% | 10% |
| Pecking | 0-80% | 80% |
| Non-absorbed yolk sac | 10-20% | 20% |
| Foot/Leg abnormalities | 10-20% | 20% |
| Navel infection | 10-20% | 20% |
| Pendulous Crop | 10-20% | 20% |
| Eye abnormalities | 5-10% | 10% |

Clinical Symptoms Associated with Infectious Bronchitis Virus:

Mortality, depression (hunched back, ruffled feathers), conjunctivitis, cough, sneezing, dyspnea, wet droppings, and vent pecking occurring post-challenge are to be expected and are not considered adverse events.

Statistical Analysis

The primary outcome is presented as categorical variable; positive or negative for IBV in tracheal swabs. Secondary variable include serum IBV titers, and trachea histopathological finding. Summary statistics for all categorical variables are reported as frequencies and percentages. All analyses are conducted per-protocol with the provision that additional statistical methods may be used to further define the nature of the endpoints and/or study variables if deemed necessary; all methods will be documented.

Results

This study was designed to evaluate the effects of a combination of probiotic *Lactobacillus reuteri* strains LR3632 and LR3630 after administration of suboptimal doses of avian coronavirus IBV vaccine. Results from the study are tabulated below in Table 14. Administration of vaccine dose at 2.8 $EID_{50}$ or 3.8 $EID_{50}$ was required in both the probiotic treated and untreated groups for any chickens to test positive for seroconversion. Probiotic Treated Group 3 showed a slightly increased fraction of animals seroconverted (70%) with suboptimal dose of 2.8×$EID_{50}$ compared to the untreated Group 7 (50%) with the same suboptimal dose of vaccine. At a higher dose of 3.8×$EID_{50}$ the treated and untreated were more similar in seroconversion rate. In this study, none of the animals (untreated or probiotic treated) showed vaccine response and seroconversion at the lowest suboptimal vaccine doses of 1.8× and 0.8×$EID_{50}$.

TABLE 14

| Sample # | Chicken ID# | Raw OD | S/P Ratio | Titer | Titer Grp | Result | GROUP | Admin | Fraction Animals Seroconverted |
|---|---|---|---|---|---|---|---|---|---|
| 7 | 217 | 0.181 | 0.024 | 100 | 0 | neg | 1 | n/a | n/a |
| 13 | 223 | 0.17 | 0 | 1 | 0 | neg | 1 | n/a | n/a |
| 14 | 224 | 0.176 | 0.01 | 42 | 0 | neg | 1 | n/a | |
| 19 | 229 | 0.181 | 0.024 | 100 | 0 | neg | 1 | n/a | n/a |
| 33 | 243 | 0.178 | 0.015 | 63 | 0 | neg | 1 | n/a | |
| 36 | 247 | 0.179 | 0.018 | 75 | 0 | neg | 1 | n/a | |
| 51 | 263 | 0.226 | 0.15 | 625 | 0 | neg | 1 | n/a | |
| 60 | 272 | 0.18 | 0.021 | 88 | 0 | neg | 1 | n/a | |
| 69 | 281 | 0.174 | 0.004 | 17 | 0 | neg | 1 | n/a | |
| 75 | 287 | 0.17 | 0 | 1 | 0 | neg | 1 | n/a | |
| 3 | 213 | 0.433 | 0.732 | 3051 | 3 | pos | 2 | 3.8 + PRO | 0.60 |
| 9 | 219 | 0.268 | 0.268 | 1117 | 1 | pos | 2 | | |
| 24 | 234 | 0.297 | 0.35 | 1459 | 1 | pos | 2 | | |
| 32 | 242 | 0.267 | 0.265 | 1105 | 1 | pos | 2 | | |
| 39 | 250 | 0.306 | 0.375 | 1563 | 1 | pos | 2 | | |
| 45 | 256 | 0.209 | 0.103 | 429 | 0 | neg | 2 | | |
| 47 | 259 | 0.241 | 0.192 | 800 | 0 | neg | 2 | | |
| 71 | 283 | 0.221 | 0.136 | 567 | 0 | neg | 2 | | |
| 80 | 292 | 0.286 | 0.319 | 1330 | 1 | pos | 2 | | |
| 82 | 294 | 0.221 | 0.136 | 567 | 0 | neg | 2 | | |
| 22 | 232 | 0.31 | 0.386 | 1609 | 1 | pos | 3 | 2.8 + PRO | 0.70 |
| 23 | 233 | 0.297 | 0.35 | 1459 | 1 | pos | 3 | | |
| 28 | 238 | 0.313 | 0.395 | 1647 | 1 | pos | 3 | | |
| 31 | 241 | 0.379 | 0.58 | 2418 | 2 | pos | 3 | | |
| 44 | 255 | 0.267 | 0.265 | 1105 | 1 | pos | 3 | | |
| 50 | 262 | 0.232 | 0.167 | 696 | 0 | neg | 3 | | |
| 57 | 269 | 0.226 | 0.15 | 625 | 0 | neg | 3 | | |
| 63 | 275 | 0.279 | 0.299 | 1246 | 1 | pos | 3 | | |
| 66 | 27 | 0.268 | 0.268 | 1117 | 1 | pos | 3 | | |
| 70 | 282 | 0.224 | 0.145 | 604 | 0 | neg | 3 | | |
| 34 | 244 | 0.197 | 0.069 | 288 | 0 | neg | 4 | 1.8 + PRO | |
| 35 | 246 | 0.173 | 0.001 | 4 | 0 | neg | 4 | | |

TABLE 14-continued

| Sample # | Chicken ID# | Raw OD | S/P Ratio | Titer | Titer Grp | Result | GROUP | Admin | Fraction Animals Seroconverted |
|---|---|---|---|---|---|---|---|---|---|
| 38 | 249 | 0.176 | 0.01 | 42 | 0 | neg | 4 | | |
| 40 | 251 | 0.189 | 0.046 | 192 | 0 | neg | 4 | | |
| 48 | 260 | 0.192 | 0.055 | 229 | 0 | neg | 4 | | |
| 49 | 261 | 0.171 | 0 | 1 | 0 | neg | 4 | | |
| 53 | 265 | 0.206 | 0.094 | 392 | 0 | neg | 4 | | |
| 65 | 277 | 0.201 | 0.08 | 333 | 0 | neg | 4 | | |
| 72 | 284 | 0.18 | 0.021 | 88 | 0 | neg | 4 | | |
| 5 | 215 | 0.201 | 0.08 | 333 | 0 | neg | 5 | 0.8 + PRO | |
| 10 | 220 | 0.176 | 0.01 | 42 | 0 | neg | 5 | | |
| 16 | 226 | 0.192 | 0.055 | 229 | 0 | neg | 5 | | |
| 25 | 235 | 0.182 | 0.027 | 113 | 0 | neg | 5 | | |
| 52 | 264 | 0.193 | 0.058 | 242 | 0 | neg | 5 | | |
| 54 | 266 | 0.187 | 0.041 | 171 | 0 | neg | 5 | | |
| 56 | 268 | 0.201 | 0.08 | 333 | 0 | neg | 5 | | |
| 77 | 289 | 0.218 | 0.128 | 534 | 0 | neg | 5 | | |
| 78 | 290 | 0.197 | 0.069 | 288 | 0 | neg | 5 | | |
| 81 | 293 | 0.186 | 0.038 | 158 | 0 | neg | 5 | | |
| 2 | 212 | 0.302 | 0.364 | 1517 | 1 | pos | 6 | 3.8 | 0.80 |
| 11 | 221 | 0.295 | 0.344 | 1434 | 1 | pos | 6 | | |
| 15 | 225 | 0.236 | 0.178 | 742 | 0 | neg | 6 | | |
| 26 | 236 | 0.284 | 0.313 | 1305 | 1 | pos | 6 | | |
| 29 | 239 | 0.443 | 0.76 | 3168 | 3 | pos | 6 | | |
| 30 | 240 | 0.317 | 0.406 | 1692 | 1 | pos | 6 | | |
| 41 | 252 | 0.304 | 0.369 | 1538 | 1 | pos | 6 | | |
| 55 | 267 | 0.287 | 0.322 | 1342 | 1 | pos | 6 | | |
| 62 | 274 | 0.206 | 0.094 | 392 | 0 | neg | 6 | | |
| 64 | 276 | 0.307 | 0.378 | 1576 | 1 | pos | 6 | | |
| 4 | 214 | 0.238 | 0.184 | 767 | 0 | neg | 7 | 2.8 | 0.50 |
| 18 | 228 | 0.212 | 0.111 | 463 | 0 | neg | 7 | | |
| 27 | 237 | 0.397 | 0.631 | 2630 | 2 | pos | 7 | | |
| 37 | 248 | 0.206 | 0.094 | 392 | 0 | neg | 7 | | |
| 43 | 254 | 0.272 | 0.279 | 1163 | 1 | pos | 7 | | |
| 59 | 271 | 0.29 | 0.33 | 1376 | 1 | pos | 7 | | |
| 73 | 285 | 0.25 | 0.218 | 909 | 1 | pos | 7 | | |
| 76 | 288 | 0.323 | 0.423 | 1763 | 1 | pos | 7 | | |
| 83 | 297 | 0.204 | 0.088 | 367 | 0 | neg | 7 | | |
| 85 | 300 | 0.183 | 0.029 | 121 | 0 | neg | 7 | | |
| 1 | 211 | 0.172 | 0 | 1 | 0 | neg | 8 | 1.8 | |
| 17 | 227 | 0.182 | 0.027 | 113 | 0 | neg | 8 | | |
| 20 | 230 | 0.173 | 0.001 | 4 | 0 | neg | 8 | | |
| 21 | 231 | 0.222 | 0.139 | 579 | 0 | neg | 8 | | |
| 42 | 253 | 0.188 | 0.044 | 183 | 0 | neg | 8 | | |
| 58 | 270 | 0.179 | 0.018 | 75 | 0 | neg | 8 | | |
| 61 | 273 | 0.174 | 0.004 | 17 | 0 | neg | 8 | | |
| 67 | 279 | 0.187 | 0.041 | 171 | 0 | neg | 8 | | |
| 79 | 291 | 0.196 | 0.066 | 275 | 0 | neg | 8 | | |
| 84 | 298 | 0.187 | 0.041 | 171 | 0 | neg | 8 | | |
| 6 | 216 | 0.187 | 0.041 | 171 | 0 | neg | 9 | 0.8 | |
| 8 | 218 | 0.19 | 0.049 | 204 | 0 | neg | 9 | | |
| 12 | 222 | 0.181 | 0.024 | 100 | 0 | neg | 9 | | |
| 46 | 258 | 0.185 | 0.035 | 146 | 0 | neg | 9 | | |
| 68 | 280 | 0.19 | 0.049 | 204 | 0 | neg | 9 | | |
| 74 | 286 | 0.17 | 0 | 1 | 0 | neg | 9 | | |

Example 7

*Lactobacillus* Probiotic Strains Impact on Lung Health

The in vivo effect of administration of *Lactobacillus reuteri* strains 3632 and 3620 for coronavirus challenge was evaluated in poultry. The immunobiotic effect of two *Lactobacillus reuteri* strains, LR3632 and LR3630, was evaluated in an avian coronavirus/infectious bronchitis (IB) virus model. The *L retueri* strains were evaluated in comparison to a *Bacillus amyloliquefaciens* strain.

Figure 6:
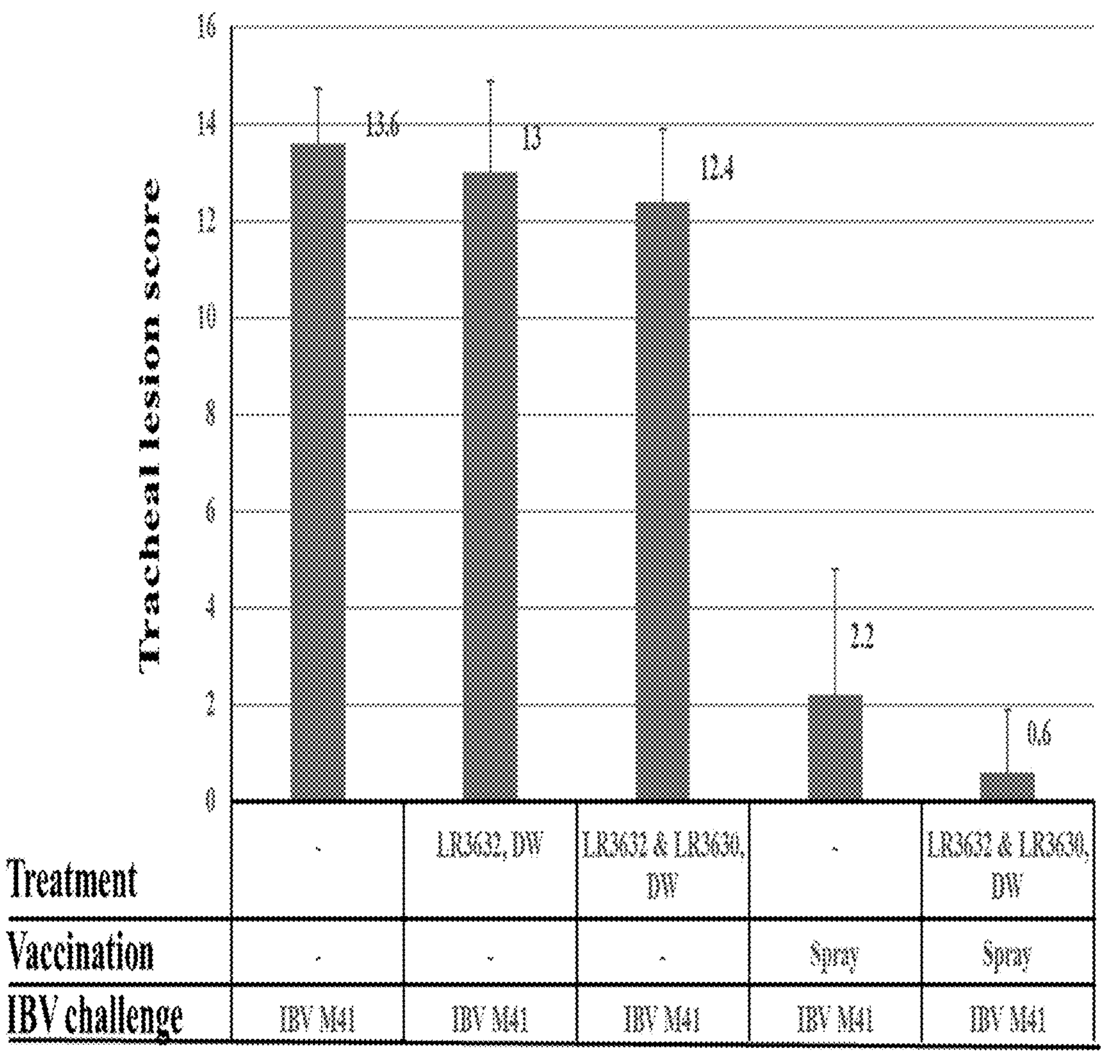
FIG. 6 depicts the effect of *L. reuteri* treatment on tracheal lesion score. Tracheal lesion score is measured and indicated on a scale of 0 to 16. Treatment (none (-), LR3632 in daily water (DW), LR3632 and LR3630 DW); Vaccination (none (-) or spray IBV); and IBV challenge (IBV M41 strain) is indicated below each tabulated result.

Day old IB vaccinated (IBV) birds+/−*Lactobacillus reuteri* (LR3632 and LR3630)+/−*Bacillus amyloliquefaciens* were challenged with IB virus on day 28. The tracheal lesion score was determined for animals treated with no administration or treated with LR3632 in daily water (DW) or LR3632 and LR3630 DW. The results are depicted in FIG. 6. Tracheal lesions were somewhat reduced with LR3632 alone and more significantly reduced with LR3632 and LR3630 in combination. LR3632 and LR3630 in combination provided reduced lesion scores even with IBV challenge versus no probiotic administration.

Figure 7:
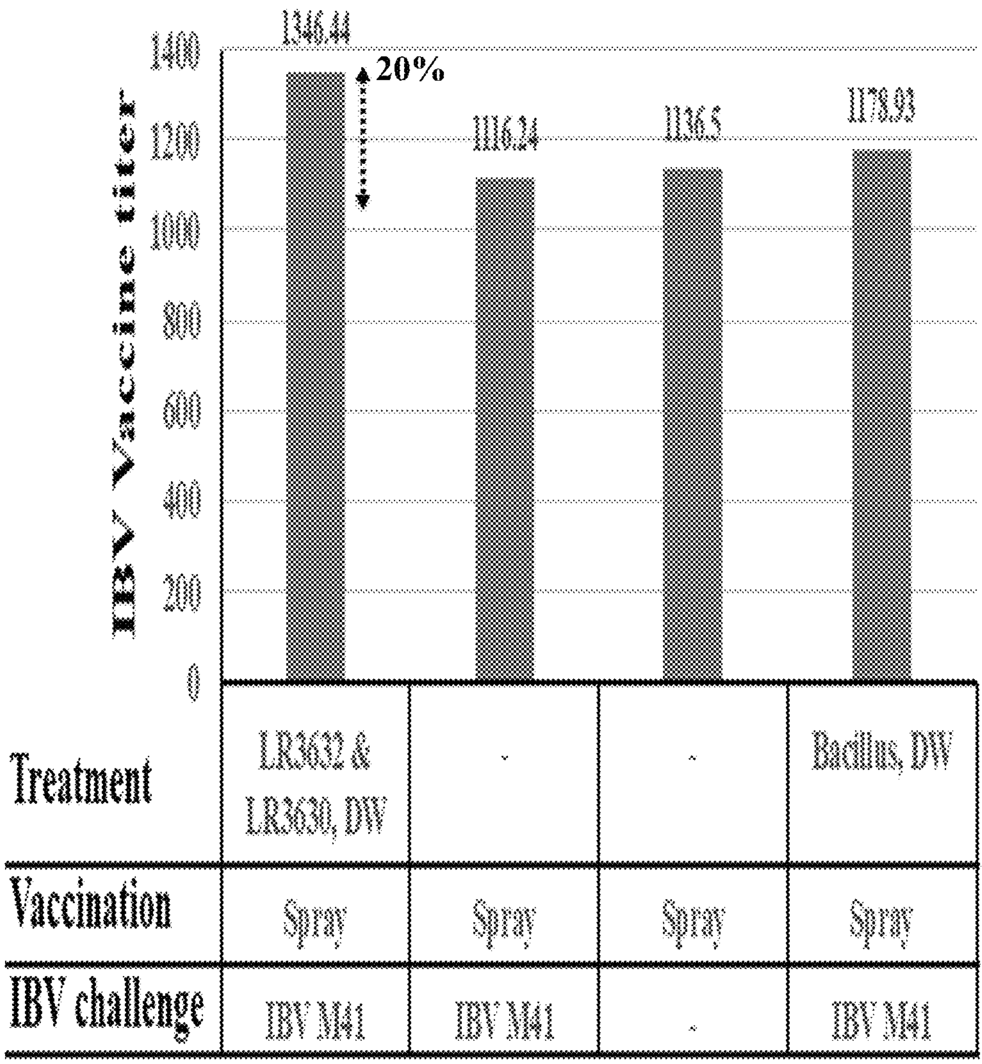
FIG. 7 depicts the effect of *L. reuteri* treatment on infectious bronchitis vaccine serology. IBV vaccine titer is measured on a scale of 0 to 1400. Treatment (none (-), LR3632 and LR3630 in daily water (DW), *Bacillus amyloliquefaciens* DW; Vaccination spray IBV; and IBV challenge (none (-) or IBV M41 strain) is indicated below each tabulated result. A 20% increase in titer with treatment LR3632 and LR3630, DW versus None (-) is indicated.

Immune response to vaccine was measured serologically using an IB specific ELISA at day 33. The effect of *L. reuteri* treatment is depicted in FIG. 7. IBV vaccine titer is measured on a scale of 0 to 1400. A 20% increase in titer was observed when animals were treated with/administered LR3632 and LR3630 DW versus controls (no treatment or administration or administered a *Bacillus amyloliquefaciens* strain.

Figure 8:
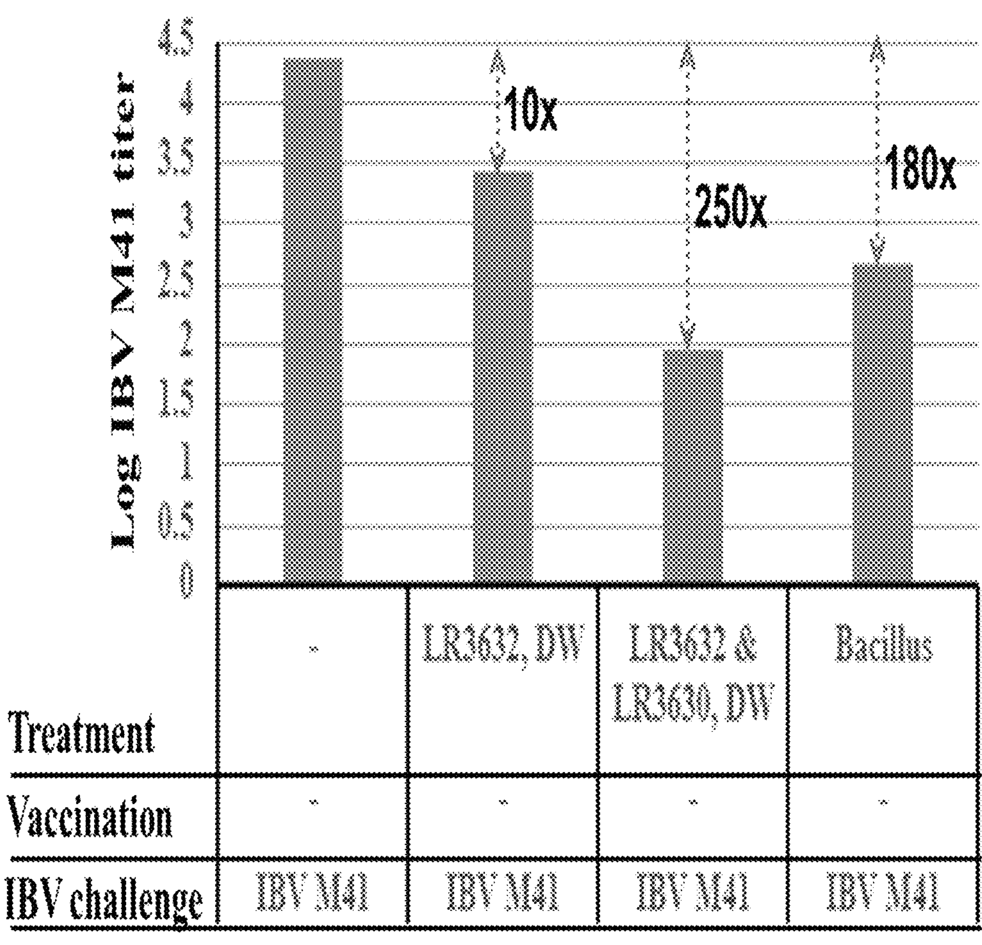
FIG. 8 depicts effect of *L. reuteri* treatment on IBV fecal viral shedding. Log IBV M41 titer is indicated on a scale of 0 to 4.5. Treatment (none (-), LR3632 in daily water (DW), LR3632 and LR3630 DW, *Bacillus amyloliquefaciens* DW; Vaccination spray IBV all None (-); and IBV challenge with IBV M41 strain is indicated below each tabulated result. Titer reductions of 10×, 250× and 180× are indicated. The combination of LR3632 and LR3630 DW provides a 250× decrease in IBV fecal viral shedding as assessed by IBV viral titer in feces.

Fecal infectious viral load was measured using quantitative PCR (qPCR). The results and Log IBV M41 titer are shown in FIG. 8. The combination of LR3632 and LR3630

DW provides a 250× decrease in IBV fecal viral shedding as assessed by IBV viral titer in feces. LR3632 reduced fecal viral shedding 10×. *Bacillus amyloliquefaciens* strain also reduced fecal virus shedding significantly.

Figure 9:
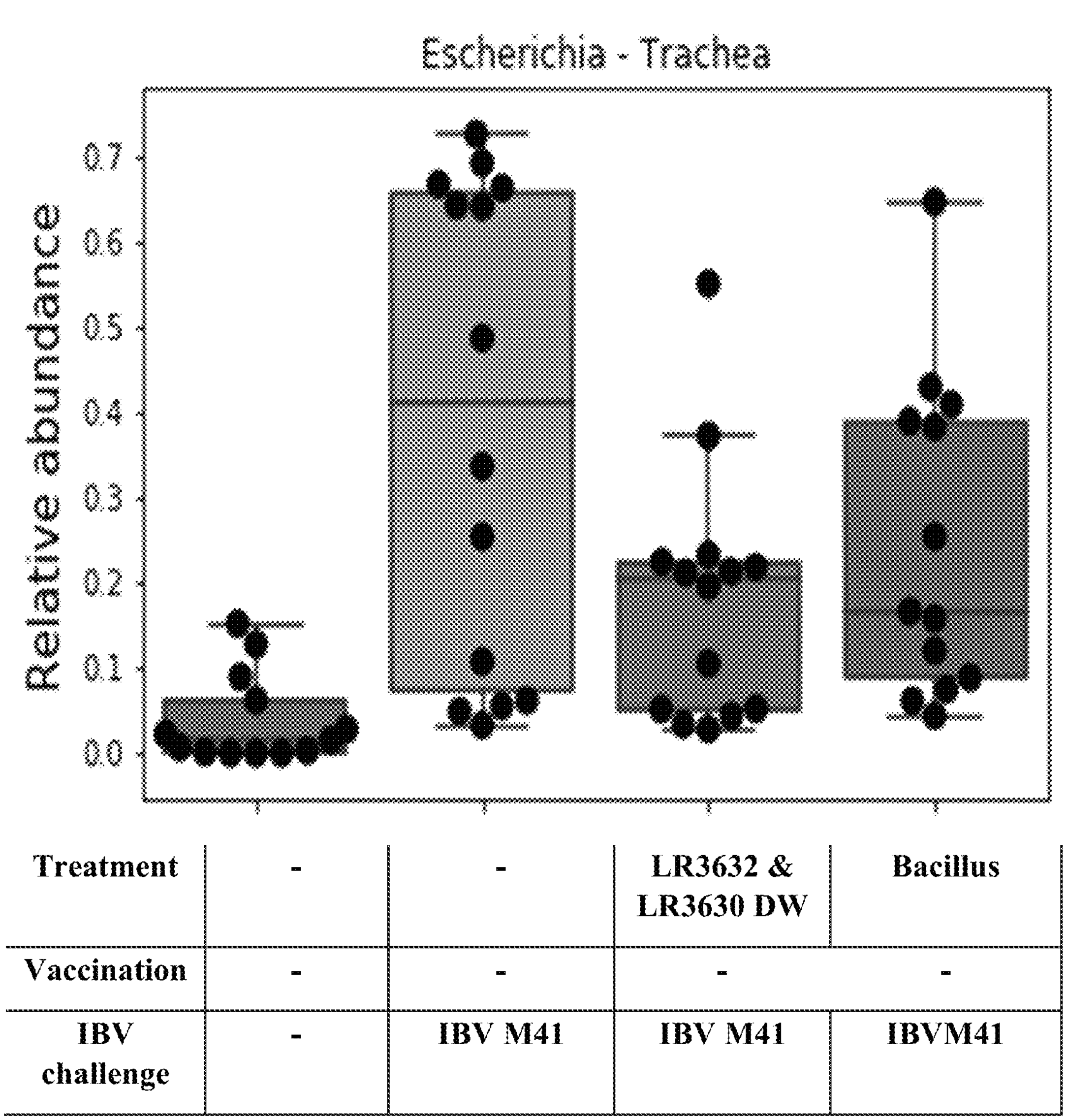
FIG. 9 depicts effect of *L. reuteri* treatment on tracheal microbiome. Relative abundance of *Escherichia* bacteria in trachea is indicated on a scale of 0.0 to 0.7. Treatment (none (-), LR3632 and LR3630 DW, *Bacillus amyloliquefaciens* DW; Vaccination spray IBV all None (-); and IBV challenge (None (-) or with IBV M41 strain) is indicated below each tabulated result.

Tracheal lesion and microbiome were evaluated. Relative abundance of *Escherichia* bacteria in trachea is depicted in FIG. 9 with no treatment or administration, a combination of LR strains 3632 and 3630, or *Bacillus amyloliquefaciens* strain. Upon challenge with IBV M41, the untreated animals had a significant increase in relative abundance of *Escherichia* in trachea, showing an altered microbiome. This is significantly reduced and controlled in poultry treated with or administered a combination of LR3632 and LR3630. *Bacillus* administered animals also showed a reduced microbiome alteration but not as significant as in the animals administered a combination of the LR3632 and LR3630 strains.

Figure 10:
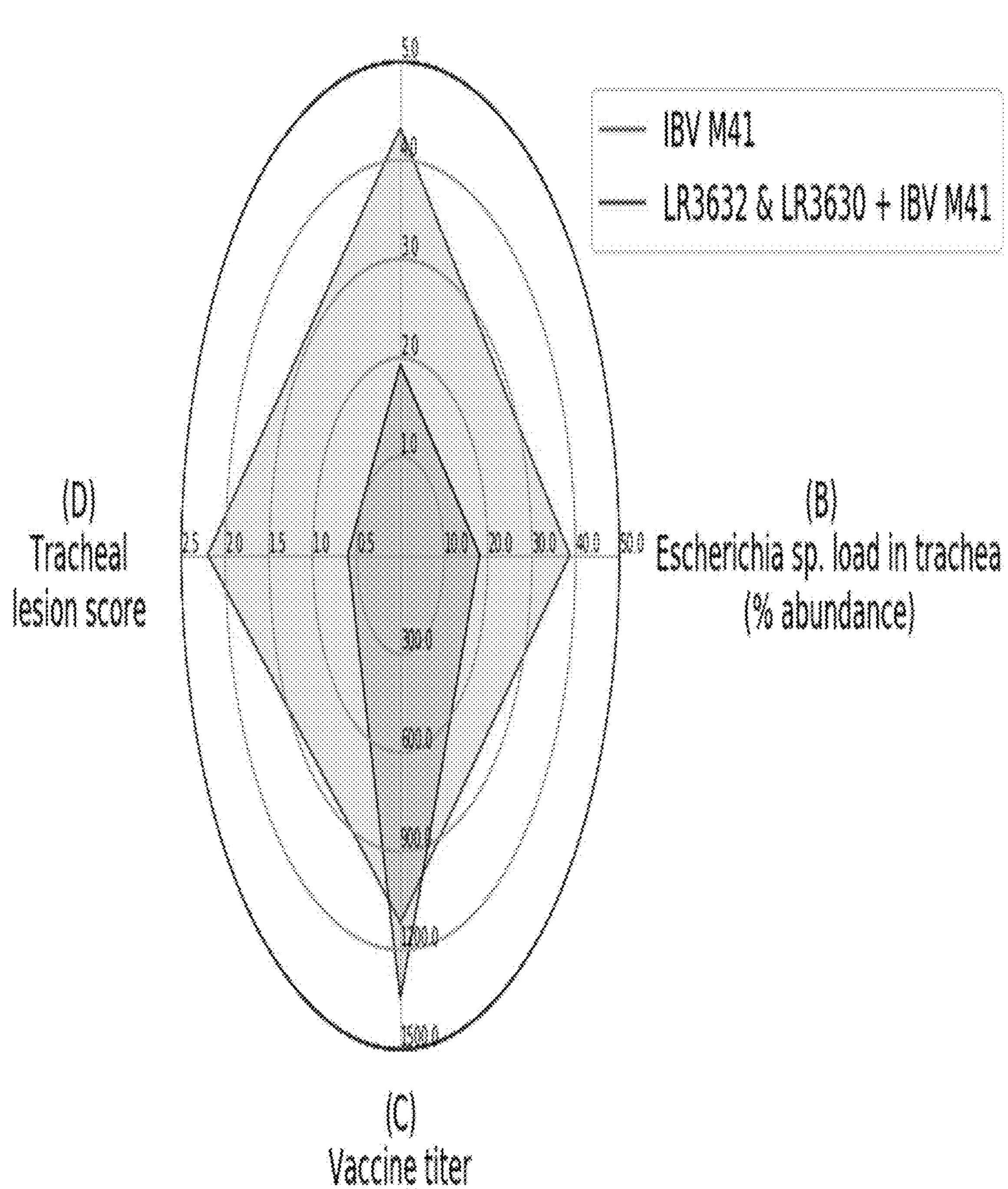
FIG. 10 depicts a graphical presentation of *Lactobacillus* impact on lung health and in vivo effect of probiotic strains LR3632 and LR3630 with coronavirus (IB) challenge in poultry. The Log 10 fecal viral shedding (A), the *Escherichia* sp. Load in trachea (B), the vaccine titre (C) and tracheal lesion score (D) are each depicted in a noted section of the graphical presentation. Scores or values with IBV M41 challenge alone and no treatment/administration of strains are indicated in red. Scores or values with IBV M41 challenge alone and prior treatment/administration of LR3632 and LR3630 strains are indicated in blue.

Overall, these studies demonstrate a reduction in viral load, positive impact on the respiratory tract microbiome, improvement in antibody titer and significant reduction of tracheal lesions in animals (poultry) administered a combination of *L. reuteri* strains LR3632 and LR3630. The overall results are depicted in a combined graphical presentation in FIG. 10. The combination of probiotic strains LR3632 and LR3630 administered along with a coronavirus vaccine in this in vivo poultry study showed improved outcomes across key metrics. The strains also had a material standalone impact on improving immunity in animals across all the metrics measured in the study.

Specific Embodiments

1. A method of stimulating an immune response in a subject, said method comprising: administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO: 1-55, and optionally, an infectious respiratory disease vaccine to a subject.
2. The method according to embodiment 1, said method comprising administering an infectious respiratory disease vaccine.
3. The method according to any one of embodiments 1-2, wherein the at least one *Lactobacillus reuteri* strain comprises at least one sequence selected from SEQ ID NO: 1-24, 26, and 49-55; and sequences having at least 98%, at least 98.5%, at least 99%, or at least 99.5% sequence identity with at least one of SEQ ID NO: 1-24, 26, and 49-55.
4. The method according to any one of embodiments 1-3, wherein the at least one *Lactobacillus reuteri* strain comprises at least one sequence selected from SEQ ID NO: 25, 27-43, and 44-48; and sequences having at least 98%, at least 98.5%, at least 99%, or at least 99.5% sequence identity with at least one of SEQ ID NO: 25, 27-43, and 44-48.
5. The method according to any one of embodiments 1-4, wherein the at least one *Lactobacillus reuteri* strain comprises an isolated first *Lactobacillus reuteri* strain comprising at least one sequence selected from SEQ ID NO: 1-24, 26, and 49-55, and an isolated second *Lactobacillus reuteri* strain comprising at least one sequence selected from SEQ ID NO: 25, 27-43, and 44-48.
6. The method according to any one of embodiments 1-5, wherein the at least one *Lactobacillus reuteri* strain comprises an isolated first *Lactobacillus reuteri* strain comprising SEQ ID NO: 49 and an isolated second *Lactobacillus reuteri* strain comprising SEQ ID NO: 44.
7. The method according to any one of embodiments 1-6, wherein the at least one *Lactobacillus reuteri* strain comprises an isolated first *Lactobacillus reuteri* strain comprising a genomic sequence as set out in any of SEQ ID NOs: 49-55 or a sequence having at least 98% or 99% or 99.5% identity to a sequence of SEQ ID NOs: 49-55 and an isolated second *Lactobacillus reuteri* strain comprising a genomic sequence as set out in any of SEQ ID NOs: 44-48 or a sequence having at least 98% or 99% or 99.5% identity to a sequence of SEQ ID NOs: 44-48.
8. The method according to any one of embodiments 1-7, wherein the at least one *Lactobacillus reuteri* strain is selected from *Lactobacillus reuteri* 3630 and *Lactobacillus reuteri* 3632.
9. The method according to any one of embodiments 1-8, wherein the at least one *Lactobacillus reuteri* strain comprises at least one of strain 3630 deposited with ATCC under patent deposit number PTA-126787 and strain 3632 deposited with ATCC under patent deposit number PTA-126788.
10. The method according to any one of embodiments 1-9, wherein the at least one *Lactobacillus reuteri* strain comprises an isolated first *Lactobacillus reuteri* strain 3632 deposited with ATCC under patent deposit number PTA-126788 comprising a genomic sequence as set out in strain PTA-126788 or a sequence having at least 98% or 99% or 99.5% identity to the genomic sequence of strain PTA-126788 and an isolated second *Lactobacillus reuteri* strain 3630 deposited with ATCC under patent deposit number PTA-126787 comprising a genomic sequence as set out in strain PTA-126787 or a sequence having at least 98% or 99% or 99.5% identity to the genomic sequence of strain PTA-126787.
11. The method according to any one of embodiments 1-10, wherein the composition comprises two *Lactobacillus reuteri* strains; and the ratio of strains is approximately 0.75-1.5:1.
12. The method according to any one of embodiments 1-11, wherein the composition comprises two *Lactobacillus reuteri* strains; and the strains are present in about equal amounts in the composition.
13. The method according to any one of embodiments 1-12, wherein said composition does not comprise a *bacillus* strain.
14. The method according to any one of embodiments 1-13, wherein said composition does not comprise *Lactobacillus buchneri, Lactobacillus plantarum, Lactobacillus gasseri, Lactobacillus johnsonii, Lactobacillus acidophilus, Lactobacillus rhamnosus, Lactobacillus paracasei*, or *Lactobacillus animalis.*
15. The method according to any one of embodiments 1-14, wherein said composition does not comprise recombinant bacteria.
16. The method according to any one of embodiments 1-15, wherein the immunogenic probiotic composition is formulated as animal feed, feed additive, food ingredient, water additive, water-mixed additive, consumable solution, consumable spray additive, consumable solid, consumable gel, injection, or combinations thereof.

17. The method according to any one of embodiments 1-16, wherein the immunogenic probiotic composition is formulated as an animal feed.

18. The method according to any one of embodiments 1-17, wherein the infectious respiratory disease vaccine is a viral vaccine.

19. The method according to any one of embodiments 1-18, wherein the infectious respiratory disease vaccine is a coronavirus vaccine, an influenza virus vaccine, an adenovirus vaccine, a parainfluenza virus vaccine, a herpesvirus vaccine, a cytomegalovirus vaccine, a respiratory syncytial vaccine, or a pneumovirus vaccine.

20. The method according to any one of embodiments 1-19, wherein the infectious respiratory disease vaccine is a coronavirus vaccine.

21. The method according to embodiment 20, wherein the coronavirus is a human coronavirus or a non-human coronavirus.

22. The method according to embodiment 21, wherein the coronavirus is a human coronavirus selected from SARS COV-2, SARS COV, MERS COV, 229E, NL63, OC43, and HKU1.

23. The method according to embodiment 21, wherein the coronavirus is a non-human coronavirus selected from infectious bronchitis virus (IBV), canine coronavirus, and feline coronavirus.

24. The method according to embodiment 23, wherein the infectious respiratory disease vaccine comprises infectious bronchitis virus (IBV) vaccine.

25. The method according to any one of embodiments 1-19, wherein the infectious respiratory disease vaccine is a Porcine Reproductive and Respiratory Syndrome (PRRS) vaccine.

26. The method according to any one of embodiments 1-19, wherein the infectious respiratory disease vaccine comprises a live attenuated vaccine, inactivated vaccine, or subunit vaccine.

27. The method according to any one of embodiments 1-19, wherein the infectious respiratory disease vaccine comprises an mRNA vaccine.

28. The method according to any one of embodiments 1-27, wherein the immunogenic probiotic composition is formulated as an animal feed, animal feed additive, water additive, or consumable spray additive.

29. The method according to any one of embodiments 1-28, wherein the immunogenic probiotic composition is administered orally and the vaccine is administered by inhalation route.

30. The method according to any one of embodiments 1-29, wherein the immunogenic probiotic composition is administered orally and the vaccine is administered by parenteral route.

31. The method according to any one of embodiments 1-30, further comprising increasing antibody titer.

32. The method according to embodiment 31, wherein the antibody titer is increased by at least 5%, at least 10%, at least 25%, at least 50%, at least 75%, or at least 100%, as compared to a subject not administered the immunogenic probiotic composition.

33. A method of vaccinating a subject for an infectious respiratory disease, said method comprising administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO:1-55, and an infectious respiratory disease vaccine to a subject.

34. The method according to embodiment 33, wherein the at least one *Lactobacillus reuteri* strain comprises an isolated first *Lactobacillus reuteri* strain comprising SEQ ID NO: 44, and an isolated second *Lactobacillus reuteri* strain comprising SEQ ID NO: 49.

35. The method according to any one of embodiments 33-34, wherein the at least one *Lactobacillus reuteri* strain comprises an isolated first *Lactobacillus reuteri* strain comprising a genomic sequence as set out in any of SEQ ID NOs: 49-55 or a sequence having at least 98% or 99% or 99.5% identity to a sequence of SEQ ID NOs: 49-55 and an isolated second *Lactobacillus reuteri* strain comprising a genomic sequence as set out in any of SEQ ID NOs: 44-48 or a sequence having at least 98% or 99% or 99.5% identity to a sequence of SEQ ID NOs: 44-48.

36. The method according to any one of embodiments 33-35, wherein the at least one *Lactobacillus reuteri* strain is selected from *Lactobacillus reuteri* 3630 and *Lactobacillus reuteri* 3632.

37. The method according to any one of embodiments 33-36, wherein the at least one *Lactobacillus reuteri* strain comprises at least one of strain 3630 deposited with ATCC under patent deposit number PTA-126787 and strain 3632 deposited with ATCC under patent deposit number PTA-126788.

38. The method according to any one of embodiments 33-37, wherein the at least one *Lactobacillus reuteri* strain comprises an isolated first *Lactobacillus reuteri* strain 3632 deposited with ATCC under patent deposit number PTA-126788 comprising a genomic sequence as set out in strain PTA-126788 or a sequence having at least 98% or 99% or 99.5% identity to the genomic sequence of strain PTA-126788 and an isolated second *Lactobacillus reuteri* strain 3630 deposited with ATCC under patent deposit number PTA-126787 comprising a genomic sequence as set out in strain PTA-126787 or a sequence having at least 98% or 99% or 99.5% identity to the genomic sequence of strain PTA-126787.

39. The method according to any one of embodiments 33-38, wherein the at least one *Lactobacillus reuteri* strain is selected from *Lactobacillus reuteri* 3630, and *Lactobacillus reuteri* 3632.

40. The method according to any one of embodiments 33-39, wherein the composition comprises two *Lactobacillus reuteri* strains; and the ratio of strains is approximately 0.75-1.5:1.

41. The method of vaccinating a subject according any one of embodiments 33-39, wherein the disease is a coronavirus associated disease.

42. The method of vaccinating a subject according to embodiment 41, wherein the disease is a feline coronavirus or canine coronavirus associated disease.

43. The method of vaccinating a subject according to any one of embodiments 33-39, wherein said infectious respiratory disease is selected from PRRS and IBV.

44. A method of increasing antibody titer in a subject, said method comprising administering an effective amount of an immunogenic probiotic composition comprising at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO:1-55, and
an infectious respiratory disease vaccine to a subject.
45. The method according to embodiment 34, wherein the at least one *Lactobacillus reuteri* strain comprises an isolated first *Lactobacillus reuteri* strain comprising SEQ ID NO: 44, and an isolated second *Lactobacillus reuteri* strain comprising SEQ ID NO: 49.
36. The method according to any one of embodiments 34-35, wherein the antibody titer is increased by at least 5%, at least 10%, at least 25%, at least 50%, at least 75%, or at least 100%, as compared to a subject not administered the composition.
37. The method according to any one of embodiments 34-36, wherein the subject is poultry, and the immunogenic probiotic composition is administered to the subject by oral administration and the infectious respiratory disease vaccine is administered by spray/inhalation.
38. The method according to any one of embodiments 34-37, wherein the subject is poultry and is at least 1 day old, at least 7 days old, or at least 14 days old.
39. A method of decreasing viral load in a subject, said method comprising administering an effective amount of an immunogenic probiotic composition comprising at least one *Lactobacillus reuteri* strain and wherein the at least one *Lactobacillus reuteri* strain comprises at least one sequence selected from SEQ ID NO:1-55 and sequences having at least 98%, at least 98.5%, at least 99%, or at least 99.5% sequence identity with at least one of SEQ ID NO: 1-55, and optionally, an infectious respiratory disease vaccine to a subject.
40. The method according to embodiment 39, wherein the at least one *Lactobacillus reuteri* strain comprises an isolated first *Lactobacillus reuteri* strain comprising SEQ ID NO: 44, and an isolated second *Lactobacillus reuteri* strain comprising SEQ ID NO: 49.
41. The method according to any one of embodiments 39-40, wherein the subject is poultry and the infectious respiratory disease vaccine is an IBV vaccine.
42. A method of stimulating an immune response in a subject, said method comprising administering an effective amount of an immunogenic probiotic composition comprising at least one *Lactobacillus reuteri* strain and wherein the at least one *Lactobacillus reuteri* strain comprises at least one sequence selected from SEQ ID NO:1-55 and sequences having at least 98%, at least 98.5%, at least 99%, or at least 99.5% sequence identity thereto, and optionally, an infectious respiratory disease vaccine to a subject.
43. The method according to embodiment 42, wherein the at least one *Lactobacillus reuteri* strain comprises
an isolated first *Lactobacillus reuteri* strain comprising at least one sequence selected from SEQ ID NO: 1-24, 26, and 49-55; and sequences having at least 98%, at least 98.5%, at least 99%, or at least 99.5% sequence identity with at least one of SEQ ID NO: 1-24, 26, and 49-55; and
an isolated second *Lactobacillus reuteri* strain comprising at least one sequence selected from SEQ ID NO: 25, 27-43, and 44-48; and sequences having at least 98%, at least 98.5%, at least 99%, or at least 99.5% sequence identity with at least one of SEQ ID NO: 25, 27-43, and 44-48.
44. The method according to any one of embodiments 42-43, wherein the at least one *Lactobacillus reuteri* strain comprises an isolated first *Lactobacillus reuteri* strain comprising a nucleic acid sequence having at least 99% identity to SEQ ID NO: 44, and an isolated second *Lactobacillus reuteri* strain comprising a nucleic acid sequence having at least 99% identity to SEQ ID NO: 49.
45. The method according to any one of embodiments 42-44, wherein the at least one *Lactobacillus reuteri* strain comprises an isolated first *Lactobacillus reuteri* strain comprising a genomic sequence as set out in any of SEQ ID NOs: 49-55 or a sequence having at least 98% or 99% or 99.5% identity to a sequence of SEQ ID NOs: 49-55 and an isolated second *Lactobacillus reuteri* strain comprising a genomic sequence as set out in any of SEQ ID NOs: 44-48 or a sequence having at least 98% or 99% or 99.5% identity to a sequence of SEQ ID NOs: 44-48.
46. The method according to any one of embodiments 42-45, wherein the at least one *Lactobacillus reuteri* strain is selected from *Lactobacillus reuteri* 3630 and *Lactobacillus reuteri* 3632.
47. The method according to any one of embodiments 42-46, wherein the at least one *Lactobacillus reuteri* strain comprises at least one of strain 3630 deposited with ATCC under patent deposit number PTA-126787 and strain 3632 deposited with ATCC under patent deposit number PTA-126788.
48. The method according to any one of embodiments 42-47, wherein the at least one *Lactobacillus reuteri* strain comprises an isolated first *Lactobacillus reuteri* strain 3632 deposited with ATCC under patent deposit number PTA-126788 comprising a genomic sequence as set out in strain PTA-126788 or a sequence having at least 98% or 99% or 99.5% identity to the genomic sequence of strain PTA-126788 and an isolated second *Lactobacillus reuteri* strain 3630 deposited with ATCC under patent deposit number PTA-126787 comprising a genomic sequence as set out in strain PTA-126787 or a sequence having at least 98% or 99% or 99.5% identity to the genomic sequence of strain PTA-126787.
49. The method according to any one of embodiments 42-48, wherein the at least one *Lactobacillus reuteri* strain is selected from *Lactobacillus reuteri* 3630, and *Lactobacillus reuteri* 3632.
50. An immunogenic probiotic composition, said composition comprising:
at least one *Lactobacillus reuteri* strain and wherein the at least one *Lactobacillus reuteri* strain comprises at least one sequence selected from SEQ ID NO: 1-55 and sequences having at least 98%, at least 98.5%, at least 99%, or at least 99.5% sequence identity with at least one of SEQ ID NO:1-55, and
a pharmaceutically acceptable carrier.
51. The composition according to embodiment 50, wherein the at least one *Lactobacillus reuteri* strain comprises at least one sequence selected from SEQ ID NO: 1-24, 26, and 49-55; and sequences having at least 98%, at least 98.5%, at least 99%, or at least 99.5% sequence identity with at least one of SEQ ID NO: 1-24, 26, and 49-55.
52. The composition according to any one of embodiments 50-51, wherein the at least one *Lactobacillus*

*reuteri* strain comprises at least one sequence selected from SEQ ID NO: 25, 27-43, and 44-48; and sequences having at least 98%, at least 98.5%, at least 99%, or at least 99.5% sequence identity with at least one of SEQ ID NO: 25, 27-43, and 44-48.

53. The composition according to any one of embodiments 50-52, wherein the at least one *Lactobacillus reuteri* strain comprises two *Lactobacillus reuteri* strains; wherein the strains comprise SEQ ID NO: 44 and SEQ ID NO: 49.

54. The composition according to any one of embodiments 50-53, wherein the at least one *Lactobacillus reuteri* strain comprises an isolated first *Lactobacillus reuteri* strain comprising a genomic sequence as set out in any of SEQ ID NOs: 49-55 or a sequence having at least 98% or 99% or 99.5% identity to a sequence of SEQ ID NOs: 49-55 and an isolated second *Lactobacillus reuteri* strain comprising a genomic sequence as set out in any of SEQ ID NOs: 44-48 or a sequence having at least 98% or 99% or 99.5% identity to a sequence of SEQ ID NOs: 44-48.

55. The composition according to any one of embodiments 50-54, wherein the at least one *Lactobacillus reuteri* strain is selected from *Lactobacillus reuteri* 3630 and *Lactobacillus reuteri* 3632.

56. The composition according to any one of embodiments 50-55, wherein the at least one *Lactobacillus reuteri* strain comprises at least one of strain 3630 deposited with ATCC under patent deposit number PTA-126787 and strain 3632 deposited with ATCC under patent deposit number PTA-126788.

57. The composition according to any one of embodiments 50-56, wherein the at least one *Lactobacillus reuteri* strain comprises an isolated first *Lactobacillus reuteri* strain 3632 deposited with ATCC under patent deposit number PTA-126788 comprising a genomic sequence as set out in strain PTA-126788 or a sequence having at least 98% or 99% or 99.5% identity to the genomic sequence of strain PTA-126788 and an isolated second *Lactobacillus reuteri* strain 3630 deposited with ATCC under patent deposit number PTA-126787 comprising a genomic sequence as set out in strain PTA-126787 or a sequence having at least 98% or 99% or 99.5% identity to the genomic sequence of strain PTA-126787.

58. The composition according to any one of embodiments 50-57, wherein the at least one *Lactobacillus reuteri* strain is selected from *Lactobacillus reuteri* 3630, and *Lactobacillus reuteri* 3632.

59. The composition according to any one of embodiments 50-58, wherein the composition comprises two *Lactobacillus reuteri* strains; and the ratio of strains is approximately 0.75-1.5:1.

60. The composition according to any one of embodiments 50-59, wherein the at least one *Lactobacillus reuteri* strain is selected from *Lactobacillus reuteri* 3630, and *Lactobacillus reuteri* 3632.

61. The composition according to any one of embodiments 50-60, wherein the *Lactobacillus reuteri* strain comprises at least one of strain 3630 deposited with ATCC under patent deposit number PTA-126787 and strain 3632 deposited with ATCC under patent deposit number PTA-126788.

62. The composition according to any one of embodiments 50-61, wherein the composition further comprises an infectious respiratory disease vaccine.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

---

SEQUENCE LISTING

The patent contains a lengthy sequence listing. A copy of the sequence listing is available in electronic form from the USPTO web site (https://seqdata.uspto.gov/docdetail?docId=US12721888B2). An electronic copy of the sequence listing will also be available from the USPTO upon request and payment of the fee set forth in 37 CFR 1.19(b)(3).

---

The invention claimed is:

1. A method of stimulating an immune response or increasing antibody titer to an infectious respiratory disease vaccine in a subject, said method comprising: administering an effective amount of an immunogenic probiotic composition comprising a combination of two Lactobacillus reuteri strains, wherein the first Lactobacillus reuteri strain comprises the genomic nucleic acid sequence SEQ ID NO: 49 or a sequence having at least 98% sequence identity with SEQ ID NO: 49, and wherein the second Lactobacillus reuteri strain comprises the genomic nucleic acid sequence SEQ ID NO: 44 or a sequence having at least 98% sequence identity with SEQ ID NO: 44, and an infectious respiratory disease vaccine to the subject.

2. The method according to claim 1, wherein the first *Lactobacillus reuteri* strain comprises SEQ ID NO: 49 and the second *Lactobacillus reuteri* strain comprises SEQ ID NO: 44.

3. The method according to claim 1, wherein the ratio of the two strains is approximately 0.75-1.5:1.

4. The method according to claim 1, wherein the first *Lactobacillus reuteri* strain is *Lactobacillus reuteri* 3632 deposited with ATCC under patent deposit number PTA-126788 and the second *Lactobacillus reuteri* strain is *Lactobacillus reuteri*3630 deposited with ATCC under patent deposit number PTA-126787.

5. The method according to claim 1, wherein said composition does not comprise *Lactobacillus buchneri, Lactobacillus plantarum, Lactobacillus gasseri, Lactobacillus*

*johnsonii, Lactobacillus acidophilus, Lactobacillus rhamnosus, Lactobacillus paracasei*, or *Lactobacillus animalis.*

6. The method according to claim 1, wherein the immunogenic probiotic composition is formulated as animal feed, feed additive, food ingredient, water additive, water-mixed additive, consumable solution, consumable spray additive, consumable solid, consumable gel, injection, or combinations thereof.

7. The method according to claim 1, wherein the infectious respiratory disease vaccine is a viral vaccine.

8. The method according to claim 7, wherein the infectious respiratory disease vaccine is a coronavirus vaccine, an influenza virus vaccine, an adenovirus vaccine, a parainfluenza virus vaccine, a herpesvirus vaccine, a cytomegalovirus vaccine, a respiratory syncytial virus vaccine, or a pneumovirus vaccine.

9. The method according to claim 8, wherein the infectious respiratory disease vaccine is a coronavirus vaccine or is a Porcine Reproductive and Respiratory Syndrome (PRRS) vaccine.

10. The method according to claim 9, wherein the coronavirus is a human coronavirus selected from SARS COV-2, SARS COV, MERS COV, 229E, NL63, OC43, and HKU1.

11. The method according to claim 9, wherein the coronavirus is a non-human coronavirus selected from infectious bronchitis virus (IBV), canine coronavirus, and feline coronavirus.

12. The method according to claim 1, wherein the immunogenic probiotic composition is administered orally and the vaccine is administered by inhalation route or by parenteral route.

13. The method according to claim 1, wherein the immune response or the antibody titer is increased by at least 5%, as compared to a subject not administered the immunogenic probiotic composition.

14. A method of vaccinating a subject for an infectious respiratory disease or decreasing viral load of an infectious respiratory disease virus in a subject, said method comprising administering an effective amount of an immunogenic probiotic composition comprising a combination of two Lactobacillus reuteri strains wherein the first Lactobacillus reuteri strain comprises the genomic nucleic acid sequence SEQ ID NO: 49 or a sequence having at least 98%, sequence identity with SEQ ID NO: 49, and wherein the second Lactobacillus reuteri strain comprises the genomic nucleic acid sequence SEQ ID NO: 44 or a sequence having at least 98% sequence identity with SEQ ID NO: 44,and an infectious respiratory disease vaccine to a subject.

15. The method according to claim 14, wherein the first *Lactobacillus reuteri* strain comprises nucleic acid sequence SEQ ID NO:49, and the second *Lactobacillus reuteri* strain comprises SEQ ID NO:44.

16. The method according to claim 14, wherein the first *Lactobacillus reuteri* strain is *Lactobacillus reuteri* strain 3632 deposited with ATCC under patent deposit number PTA-126788, and the second Lactobacillus reuteri strain is *Lactobacillus reuteri* strain 3630 deposited with ATCC under patent deposit number PTA-126787.

17. The method according to claim 14, wherein the ratio of the two strains is approximately 0.75-1.5:1.

18. The method according to claim 14, wherein the infectious respiratory disease is a coronavirus associated disease, an influenza virus associated disease, an adenovirus associated disease, a parainfluenza virus associated disease, a herpesvirus associated disease, a cytomegalovirus associated disease, a respiratory syncytial virus associated disease, or a pneumovirus associated disease.

19. The method according to claim 14, wherein the disease is a feline coronavirus or canine coronavirus associated disease.

20. The method according to claim 14, wherein said infectious respiratory disease is selected from PRRS and IBV.

21. The method according to claim 1, wherein the subject is poultry, and the immunogenic probiotic composition is administered to the subject by oral administration and the infectious respiratory disease vaccine is administered by spray/inhalation.

22. The method according to claim 21, wherein the subject is poultry and is at least 1 day old.

23. The method according to claim 14, wherein the subject is poultry and the infectious respiratory disease vaccine is an IBV vaccine.

24. The method according to claim 1, wherein the first *Lactobacillus reuteri* strain comprises a nucleic acid sequence having at least 99% identity to SEQ ID NO: 49, and the second *lactobacillus reuteri* strain comprises a nucleic acid sequence having at least 99% identity to SEQ ID NO: 44.

25. An immunogenic probiotic composition, said composition comprising a combination of two *Lactobacillus reuteri* strains, wherein the first *Lactobacillus reuteri* strain comprises the genomic nucleic acid sequence SEQ ID NO: 49 or a sequence having at least 98%, sequence identity with SEQ ID NO: 49, and wherein the second *Lactobacillus reuteri* strain comprises the genomic nucleic acid sequence SEQ ID NO: 44 or a sequence having at least 98% sequence identity with SEQ ID NO: 44, a pharmaceutically acceptable carrier, and an infectious respiratory disease vaccine.

26. The composition according to claim 25, wherein the first *Lactobacillus reuteri* strain comprises SEQ ID NO: 49 and the second *Lactobacillus reuteri* strain comprises SEQ ID NO: 44.

27. The composition according to claim 25, wherein the ratio of the two strains is approximately 0.75-1.5:1.

28. The composition according to claim 25, wherein the first *Lactobacillus reuteri* strain is *Lactobacillus reuteri* strain 3632 deposited with ATCC under patent deposit number PTA-126788, and the second *Lactobacillus reuteri* strain is Lactobacillus reuteri strain 3630 deposited with ATCC under patent deposit number PTA-126787.

29. The method according to claim 13, wherein the immune response or the antibody titer is increased by at least 10%.

30. The method according to claim 14, wherein the first *Lactobacillus reuteri* strain comprises a genomic nucleic acid sequence having at least 99% sequence identity with SEQ ID NO: 49, and the second *Lactobacillus reuteri* strain comprises a genomic nucleic acid sequence having at least 99% sequence identity with SEQ ID NO: 44.

31. The immunogenic probiotic composition according to claim 25, wherein the first *Lactobacillus reuteri* strain comprises a genomic nucleic acid sequence having at least 99% sequence identity with SEQ ID NO: 49, and the second *Lactobacillus reuteri* strain comprises a genomic nucleic acid sequence having at least 99% sequence identity with SEQ ID NO: 44.

* * * * *